US009332895B2

(12) United States Patent
Kikuchi

(10) Patent No.: US 9,332,895 B2
(45) Date of Patent: May 10, 2016

(54) LIGHT IRRADIATING APPARATUS

(75) Inventor: Satoru Kikuchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1027 days.

(21) Appl. No.: 13/449,820

(22) Filed: Apr. 18, 2012

(65) Prior Publication Data
US 2012/0200687 A1 Aug. 9, 2012

Related U.S. Application Data

(63) Continuation of application No. PCT/JP2010/063633, filed on Aug. 11, 2010.

(30) Foreign Application Priority Data

Oct. 21, 2009 (JP) ................................ 2009-242625

(51) Int. Cl.
*A61B 1/06* (2006.01)
*F21V 9/00* (2015.01)
(Continued)

(52) U.S. Cl.
CPC .................. *A61B 1/041* (2013.01); *A61B 1/043* (2013.01); *A61B 1/0638* (2013.01);
(Continued)

(58) Field of Classification Search
USPC ............ 600/160, 178, 180; 362/84, 231, 230, 362/97.3, 800, 249.02; 348/68
See application file for complete search history.

(56) References Cited

U.S. PATENT DOCUMENTS 7,938,550 B2   5/2011   Takenaka
8,790,253 B2 * 7/2014   Sunagawa ............ A61B 1/0638
                                                        362/227
(Continued)

FOREIGN PATENT DOCUMENTS

CN      101320727 A    12/2008
EP      1 749 871 A1    2/2007
(Continued)

OTHER PUBLICATIONS

International Search Report dated Nov. 16, 2010 (in English) in counterpart International Application No. PCT/JP2010/063633.
(Continued)

*Primary Examiner* — Thomas J Sweet
*Assistant Examiner* — Arnaldo Torres Diaz
(74) *Attorney, Agent, or Firm* — Holtz, Holtz & Volek PC

(57) ABSTRACT

A light source apparatus is designed in accordance with an object, and following elements and phosphors are disposed in a casing, a first light emitting element that emits a light in a first irradiation mode, which is selected so that a light emission band has a portion that overlaps a first-specific-band, a first phosphor selected so as to include the first-specific-band in an excitation band and include a second-specific-band in a fluorescence-emission-band, a second phosphor selected so that an excitation intensity compared with the first phosphor is low in the first-specific-band, and high in a second-fluorescence-excitation-band at a short wavelength side in a second-irradiation-band and a fluorescence-emission-band includes the second-irradiation-band other than the second-fluorescence-excitation-band, and a second light emitting element that emits a light in a second irradiation mode, which is selected so that a light emission band is included in the second-fluorescence-excitation-band.

12 Claims, 14 Drawing Sheets

(51) Int. Cl.
*A61B 1/04* (2006.01)
*H01L 33/50* (2010.01)
*H01L 25/075* (2006.01)

(52) U.S. Cl.
CPC ............ *A61B 1/0653* (2013.01); *A61B 1/0692* (2013.01); *H01L 33/504* (2013.01); *H01L 25/0753* (2013.01); *H01L 2224/45144* (2013.01); *H01L 2224/48091* (2013.01)

(56) References Cited

U.S. PATENT DOCUMENTS

| | | | |
|---|---|---|---|
| 2005/0215911 A1* | 9/2005 | Alfano | A61B 1/041 600/476 |
| 2006/0227302 A1 | 10/2006 | Harbers et al. | |
| 2007/0023734 A1 | 2/2007 | Igarashi et al. | |
| 2008/0030984 A1 | 2/2008 | Harbers et al. | |
| 2008/0128740 A1 | 6/2008 | Yamashita et al. | |
| 2009/0040781 A1* | 2/2009 | Ito | A61B 1/0653 362/554 |
| 2009/0062617 A1 | 3/2009 | Mizuyoshi | |
| 2009/0167149 A1* | 7/2009 | Ito | A61B 1/0638 313/501 |
| 2009/0303319 A1 | 12/2009 | Sato et al. | |
| 2015/0022998 A1* | 1/2015 | Tao | F21V 9/16 362/84 |
| 2015/0116983 A1* | 4/2015 | Narendran | F21K 9/00 362/84 |

FOREIGN PATENT DOCUMENTS

| | | |
|---|---|---|
| EP | 1 911 389 A1 | 4/2008 |
| EP | 2 030 559 A1 | 3/2009 |
| EP | 2 074 934 A2 | 7/2009 |
| EP | 2 127 592 A1 | 12/2009 |
| JP | 2007-036041 A | 2/2007 |
| JP | 2007-036042 A | 2/2007 |
| JP | 2008-085026 A | 4/2008 |
| JP | 2008-305992 A | 12/2008 |
| JP | 2009-153712 A | 7/2009 |
| WO | WO 2007/018098 A1 | 2/2007 |
| WO | WO 2008/102803 A1 | 8/2008 |

OTHER PUBLICATIONS

Extended European Search Report (EESR) dated Aug. 3, 2012 (in English) in counterpart European Application No. 10824719.8.
Chinese Office Action dated May 6, 2014 in counterpart Chinese Application No. 201080047200.2.
Japanese Office Action dated May 7, 2013 issued in counterpart Japanese Application No. 2009-242625.

* cited by examiner

LIGHT IRRADIATING APPARATUS

CROSS REFERENCE TO RELATED APPLICATION

This application is a continuation application of PCT/JP2010/063633 filed on Aug. 11, 2010 and claims benefit of Japanese Application No. 2009-242625 filed in Japan on Oct. 21, 2009, the entire contents of which are incorporated herein by this reference.

BACKGROUND OF THE INVENTION

1. Field of the Invention

The present invention relates to a light source apparatus which emits lights with different spectrums in a plurality of irradiation modes, an electronic image acquiring apparatus, an electronic image observation apparatus, an endoscope apparatus and a capsule endoscope apparatus which include the light source apparatus.

2. Description of the Related Art

Some objects perform optically characteristic behaviors in certain specific spectrum bands (hereinafter, "spectrum band" will be simply described as "band" where appropriate). The term optically characteristic behaviors in this case means exhibition of optical properties different from the optical properties in other bands, in specific bands. As a specific example, a peak and a bottom (minimum) of an absorption spectrum, a peak and a bottom of a reflection spectrum, a peak and a bottom of an excitation spectrum in fluorescence emission, and the like can be cited.

When such an object is irradiated with a light of a wavelength included in the specific band, the object to be observed can be clearly observed by being separated from the other objects. Observation like this has been conventionally known as NBI (Narrow Band Imaging) observation.

Among the objects which perform optically characteristic behaviors, some objects each have the presence of two or more specific bands, and hemoglobin is cited as an example. More specifically, hemoglobin has two peaks of absorption spectrum when the hemoglobin is either hemoglobin Hb or oxyhemoglobin HbO2 as shown in FIG. 5 according to an embodiment of the present invention. Here, a first absorption spectrum peak P1 is present at approximately 415 nm, and a second absorption spectrum peak P2 is present at approximately 540 nm Hemoglobin is distributed mainly in a blood vessel since hemoglobin is included in a red blood corpuscle which is one of main components of blood, and is not basically distributed in somatic cells. Therefore, if NBI observation is performed, an image of blood vessel portions is picked up with a low luminance, whereas images of the portions other than the blood vessel portions are picked up with a high luminance, and an image in which the blood vessel portions are emphasized with respect to the portions other than the blood vessels can be acquired.

The light of a band around 415 nm in the specific band of hemoglobin described above is reflected with a relatively high reflectivity or scattered in a surface layer (stratum mucosum and the like) of a body tissue 100, and has a low penetrance to an inner portion of the body tissue 100 as shown in FIG. 3 relating to the embodiment of the present invention, and therefore, is suitable for observation of a distribution of a blood vessel 101 located in the surface layer of the body tissue 100. Meanwhile, a light of a band around 540 nm penetrates to the inner portion of the body tissue 100 more deeply than the light of the band around 415 nm, and reflected or scattered in the inner portion from the surface layer of the body tissue 100 as shown in FIG. 4 according to the embodiment of the present invention, and therefore is suitable for observation of the distribution of the blood vessel 101 in a deeper portion than the surface layer of the body tissue 100. Accordingly, with use of both the light of the band around 415 nm and the light of the band around 540 nm, an image (blood vessel-emphasized image) in which contrast enhancement of the blood vessel 101 located in the surface layer of the body tissue 100 and contrast enhancement of the blood vessel 101 located in the deeper portion than the surface layer are simultaneously applied can be acquired and observed.

If a light of another wavelength is present other than the light of the band around 415 nm and the light of the band around 540 nm relating to the specific band at this time, the contrast of the blood vessel 101 and the body tissue 100 other than the blood vessel is weakened, and therefore, it is desirable that a light of the band other than the specific band does not coexist when NBI observation is performed.

As an example of use of the specific band in the absorption spectrum of hemoglobin, a clinical example of use in discovering a cancer tissue in the medical field is cited. More specifically, a cancer tissue differs in the disposition structure of blood vessels from a normal site, and therefore, a cancer tissue can be easily discovered by clear observation of the structure of blood vessels with use of NBI. In such an inspection, ordinary observation by a white color light, for example, can be desirably performed besides observation by NBI.

In order to enable a first irradiation mode according to NBI irradiation that is irradiation at a time of NBI observation, and a second irradiation mode of performing irradiation by a white color light or the like as above, a plurality of light source apparatuses corresponding to the respective irradiation modes are conventionally required, and further, there is the case in which a plurality of light source apparatuses are further required in one irradiation mode (for example, the case in which light source apparatuses of respective colors of R, G and B are required respectively to obtain a white color light, the case in which light source apparatuses corresponding to the number of specific bands are required in NBI observation, or the like).

A light emitting apparatus that can emit a plurality of lights with different spectrums is described in, for example, Japanese Patent Application Laid-Open Publication No. 2007-36042. The light emitting apparatus described in the Publication has a first light source disposed on a bottom surface of a casing which forms, for example, a bottomed cylindrical shape, and has a partition wall disposed in a central portion of the casing so that the lights of the first light source reaches both sides. Furthermore, a number of first phosphors are disposed with use of a filler on one side separated with the partition wall, and a number of second phosphors are disposed with use of a filler on the other side. Here, the first phosphor and the second phosphor both include the emission band of the first light source in excitation bands. Further, the first phosphor and the second phosphor have main fluorescence emission bands at a long wavelength side as compared with the emission band of the first light source, and the fluorescence emission bands are different bands from each other. Here, if the first phosphor is a green color phosphor, the second phosphor is a red color phosphor, and a green color light is included in the excitation band of the red color phosphor, the green color light which is fluorescently emitted from the green color phosphor may be used in excitation of the red color phosphor if a partition wall is not provided. Thus, the partition wall is provided as described above, and reduction in the light emission efficiency is prevented. Consequently, according to the art described in the Publication, three kinds of lights, which are the light of the first light source, the light which is fluorescently emitted from the first phosphor, and the light which is fluorescently emitted from the second phosphor are simultaneously emitted. In the art of the Publication, the first phosphor and the second phosphor are disposed at the positions spatially different from each other with the partition wall therebetween, and therefore, when the respective phosphors are regarded as point light sources, the respective phosphors are optically separated (regarded as two point light sources). When the light emitting apparatus including the structure separated into two as above is used as one point light source, an optical element or the like which sufficiently mixes lights is considered to be additionally required.

Further, Japanese Patent Application Laid-Open Publication No. 2007-36041 describes a configuration in which at one side in a casing separated with a partition wall, a first light source and a phosphor are disposed with use of a filler, and at the other side, a second light source is disposed with use of a filler. According to the art described in the Publication, three kinds of lights that are a light of the first light source, a light which is fluorescently emitted from the phosphor, and a light of the second light source can be emitted. Structurally, simultaneous emission of the three kinds of lights is enabled, and time-division emission of the lights of the first light source and the phosphor, and the light of the second light source is enabled. The art of the Publication is also of the structure in which the first light source and the second light source are disposed with the partition wall therebetween, and therefore, is also optically separated, and it is conceivable that when the light sources are used as one point light source, an optical element or the like which sufficiently mixes the lights is additionally required.

SUMMARY OF THE INVENTION

A light source apparatus according to first aspect of the present invention is a light source apparatus emitting a light of a first specific spectrum band (hereinafter, "spectrum band" will be simply described as "band") and a light of a second specific band with a wavelength longer than the first specific band in a first irradiation mode, and emitting a light of a second irradiation band with a spectrum different from the light in the first irradiation mode, in a second irradiation mode, and includes a casing that is opened toward an irradiating direction of the light, a first light emitting element that is provided in the casing, emits the light in the first irradiation mode, and does not emit the light in the second irradiation mode, with a light emission band having a portion that overlaps the first specific band, a first phosphor that is provided in the casing so that the light emitted by the first light emitting element can reach the first phosphor, includes the first specific band in an excitation band, and includes the second specific band in a fluorescence emission band, a second phosphor that is provided in the casing so that the light emitted by the first light emitting element reaches the second phosphor, with an excitation intensity compared with the first phosphor being low in the first specific band, and high in a second fluorescence excitation band at a short wavelength side in the second irradiation band, and with a fluorescence emission band including the second irradiation band other than the second fluorescence excitation band, and a second light emitting element that is provided in the casing so that an emitted light can reach the first phosphor and the second phosphor, emits the light in the second irradiation mode, and does not emit the light in the first irradiation mode, with a light emission band being included in the second fluorescence excitation band.

Further, an electronic image acquiring apparatus according to second aspect of the present invention includes the above described light source apparatus, and an image pickup apparatus that causes a light irradiated from the light source apparatus and reflected by an object to form an image by an optical system and picks up the image.

Furthermore, an electronic image observation apparatus according to third aspect of the present invention includes the above described electronic image acquiring apparatus, and a display apparatus that displays an image picked up by the image pickup apparatus.

Further, an endoscope apparatus according to forth aspect of the present invention includes the above described electronic image acquiring apparatus, and an insertion portion in which an irradiating optical element for irradiating an object with the light from the light source apparatus, and an observing optical element configuring at least a part of the optical system of the image pickup apparatus are disposed at a distal end side.

In addition, a capsule endoscope apparatus according to fifth aspect of the present invention includes the above described electronic image acquiring apparatus, and a capsule casing that houses the electronic image acquiring apparatus.

DETAILED DESCRIPTION OF THE PREFERRED EMBODIMENT

Hereinafter, an embodiment of the present invention will be described with reference to the drawings.

Embodiment 1

FIG. 1 to FIG. 22 show embodiment 1 of the present invention.

A light source apparatus 1 of the present embodiment is configured to emit a light of a first specific spectrum band (Hereinafter, "spectrum band" will be simply described as "band") and a light of a second specific spectrum band of a wavelength longer than the first specific band as a first irradiation mode, and emit a light which is not dependent on the respective specific spectrum bands in the first irradiation mode as a second irradiation mode.

Here, "specific band" means a band in which an optically characteristic behavior occurs in an object, or an irradiation band suitable for observation with emphasis placed on a specific color of the object.

Further, the second specific band having a "longer wavelength" than the first specific band means that the shortest wavelength of the wavelengths included in the second specific band is longer than the longest wavelength of the wavelengths included in the first specific band. Accordingly, it can be said that the first specific band and the second specific band are separated in terms of band.

As above, the first irradiation mode is an irradiation mode of performing irradiation of a light in a band in which an optically characteristic behavior occurs in an object, or an irradiation band suitable for observation with emphasis on a specific color of the object. In contrast with this, the second irradiation mode is an irradiation mode of by emitting a light with a different spectrum from the first irradiation mode, and performing irradiation of a light which is not dependent on the specific band in the first irradiation mode. However, the second irradiation mode only intends to be independent on the first and the second specific bands in the aforementioned first irradiation mode, and may be an irradiation mode of emitting a light of another specific band different from the first and the second specific bands. More specifically, in the second irradiation mode, irradiation of a light may be performed in a band in which an optically characteristic behavior occurs in an object, or an irradiation band suitable for observation with emphasis on a specific color of the object.

Here, NBI (Narrow Band Imaging) irradiation which is one example of the first irradiation mode will be first described with reference to FIG. 3 to FIG. 5. Here, FIG. 3 is a view showing a state in which a light of a band around 415 nm is reflected in a body tissue including a blood vessel, FIG. 4 is a view showing a state in which a light of a band around 540 nm is reflected in a body tissue including a deep blood vessel, and FIG. 5 is a diagram showing absorption spectrums of hemoglobin Hb and oxyhemoglobin HbO2.

Figure 5:
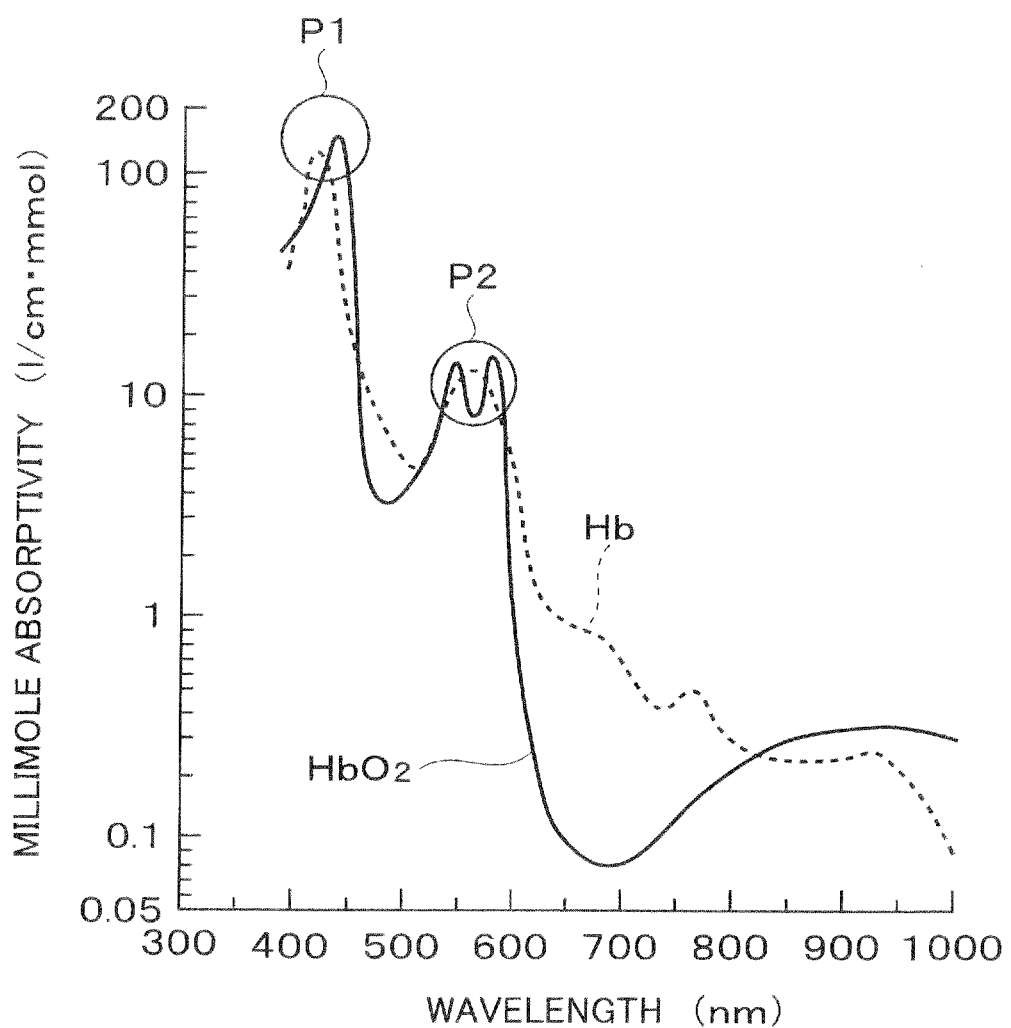
FIG. 5 is a diagram showing absorption spectrums of hemoglobin Hb and oxyhemoglobin HbO2, in the above described embodiment 1.

As described above, hemoglobin has two peaks of the absorption spectrum as shown in FIG. 5, when the hemoglobin is hemoglobin Hb or oxyhemoglobin HbO2. Here, a first absorption spectrum peak P1 is present at approximately 415 nm, and a second absorption spectrum peak P2 is present at approximately 540 nm. In the example, the band around 415 nm can be regarded as the above described first specific band, and the band around 540 nm can be regarded as the above described second specific band.

Figure 3:
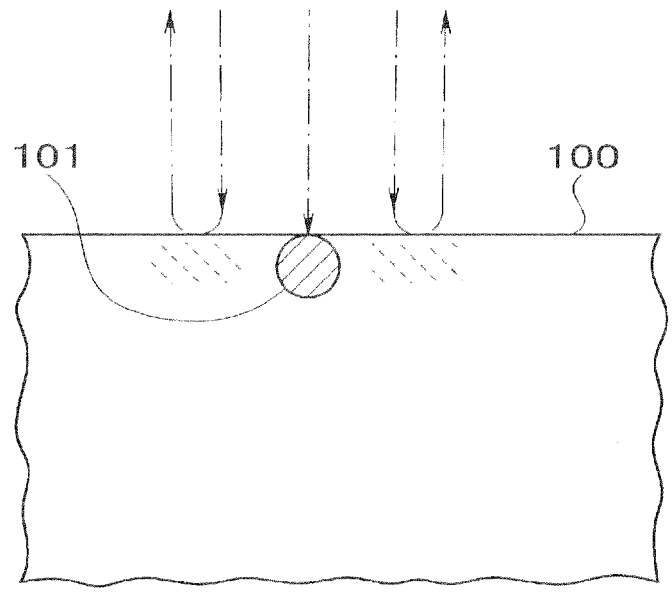
FIG. 3 is a view showing a state in which a light of a band around 415 nm is reflected in the body tissue including a blood vessel, in the above described embodiment 1.

The light of the first specific band around 415 nm of the above bands is reflected at a relatively high reflectivity or scattered in a surface layer (stratum mucosum and the like) of a body tissue 100, as shown in FIG. 3, and has a low penetrance to an inner portion of the body tissue 100. Accordingly, the light of the first specific band is suitable for observation of a distribution of a blood vessel 101 located in the surface layer of the body tissue 100.

Figure 4:
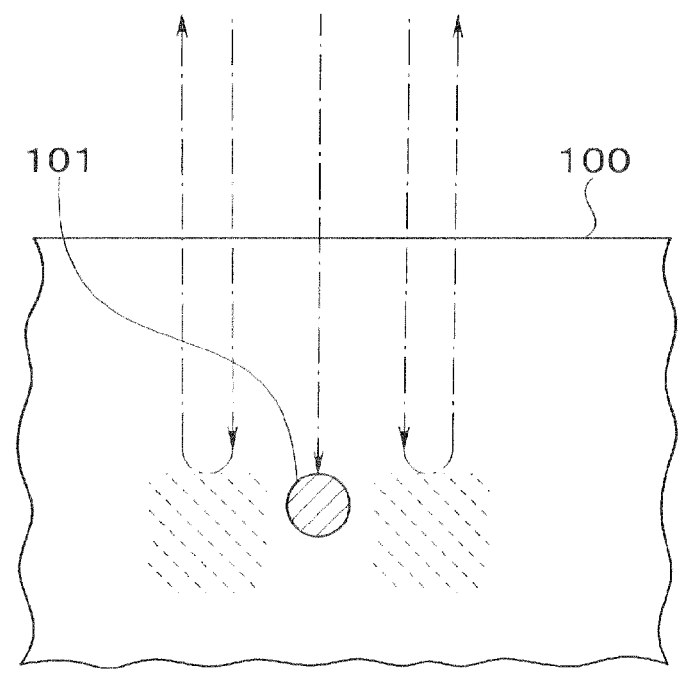
FIG. 4 is a view showing a state in which a light of a band around 540 nm is reflected in the body tissue including a deep blood vessel, in the above described embodiment 1.

Meanwhile, the light of the second specific band around 540 nm penetrates to the inner portion of the body tissue 100 more deeply than the light of the first specific band, and is reflected or scattered in the inner portion from the surface layer of the body tissue 100, as shown in FIG. 4. Accordingly, the light of the second specific band is suitable for observation of the distribution of the blood vessel 101 which is located in a deeper portion than the surface layer of the body tissue 100.

As above, with use of both the light of the first specific band and the light of the second specific band, the blood vessel 101 located in the surface layer of the body tissue 100 and the blood vessel 101 located in the deeper portion than the surface layer can be simultaneously observed.

However, if a light of a wavelength other than the lights of the first and the second specific bands is present at this time, the contrast of the blood vessel 101 and the body tissue 100 other than the blood vessels becomes weak.

Thus, when NBI observation is performed, only the light of the narrow band around 415 nm and the light of the narrow band around 540 nm are irradiated as much as possible.

Further, as an example of the second irradiation mode in the case of NBI irradiation being performed as the first irradiation mode, white color irradiation is cited. The white color irradiation is a typical example of irradiation for use in normal light imaging.

The number of specific bands in the first irradiation mode is not limited two as a matter of course, and may be three or more. More specifically, even when the first irradiation mode has three or more specific bands, a combination of optional two can be configured as described as follows.

Further, here, as an example of the specific band, the example of two intensity peaks of the absorption spectrum is cited, but the specific band is not limited to the example. For example, the specific band may be the combination of optional two or more (may be of the same kind) of bands which exist for the object and where optically characteristic behaviors occur to the object, that is, an intensity peak of the absorption spectrum, an intensity peak of a reflection spectrum, an intensity peak of the excitation spectrum in fluorescence emission (for example, fluorescence emission by spontaneous light emission of the object, fluorescence emission by light emission of a fluorescent agent by introduction of the fluorescent agent into the object, or the like) and the like.

Further, the specific band is not limited to a band in which an optically characteristic behavior occurs. For example, the case may be applied, in which in order to observe an object including two or more areas where reflection spectrums do not overlap each other in colors emphasizing the respective areas (for example, preferable colors corresponding to the respective areas), irradiation is performed with two or more specific bands.

Figure 6:
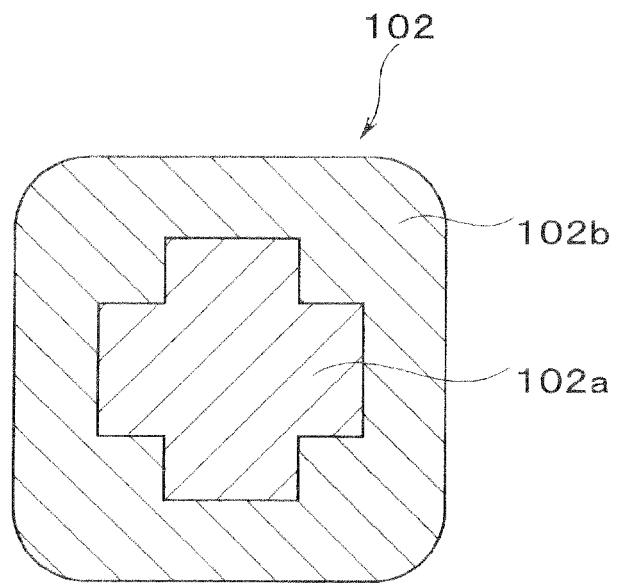
FIG. 6 is a view showing an example of an object including two areas in which reflection spectrums do not overlap each other, in the above described embodiment 1.

The case as above will be described with reference to FIG. 6 and FIG. 7. Here, FIG. 6 is a view showing an example of an object including two areas in which reflection spectrums do not overlap each other, and FIG. 7 is a diagram showing an example of the spectrum at the time of irradiation of the object of FIG. 6 with lights of two bands which individually overlap the respective reflection spectrums.

Figure 7:
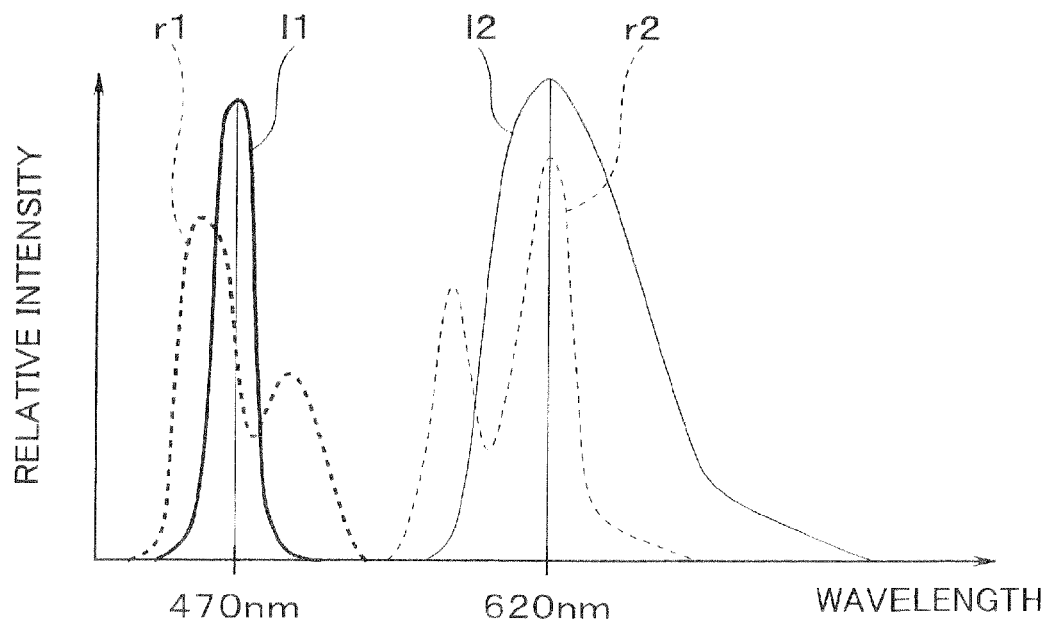
FIG. 7 is a diagram showing an example of spectrums when the object of FIG. 6 is irradiated with lights of two bands which individually overlap the respective reflection spectrums, in the above described embodiment 1.

An object 102 includes a first area 102a in which an intensity of a reflection spectrum r1 exists only in a band of a blue color around 470 nm, and a second area 102b in which an intensity of a reflection spectrum r2 exists only in a band of a red color around 620 nm, and the band of the reflection spectrum r1 and the band of the reflection spectrum r2 are assumed not to overlap each other as shown in FIG. 7.

It is assumed that the object 102 as above is irradiated with a light of a light emission spectrum 11 (for example, a narrow band light having a peak of light emission intensity at, for example, 470 nm) which overlaps the band of the reflection spectrum r1, but does not overlap the band of the reflection spectrum r2, and a light of a light emission spectrum 12 (for example, a light having a peak of a light emission intensity at, for example, 620 nm) which overlaps the band of the reflection spectrum r2, but does not overlap the band of the reflection spectrum r1, simultaneously with the same directional characteristics, as the lights of the specific bands. Thereupon, both the first area 102a and the second area 102b are irradiated with the light of the light emission spectrum 11, but the light of the light emission spectrum 11 is reflected on only the first area 102a, and is not reflected on the second area 102b. Similarly, both the first area 102a and the second area 102b are irradiated with the light of the light emission spectrum 12, but the light of the light emission spectrum 12 is reflected on only the second area 102b, and is not reflected on the first area 102a.

Thereby, in the first area 102a, the color of the band of the light emission spectrum 11 is especially emphasized in the reflection spectrum r1 band. Further, in the second area 102b, the color of the band of the light emission spectrum 12 is especially emphasized in the reflection spectrum r2 band. Accordingly, observation with the colors of the respective areas emphasized in accordance with the respective areas is enabled.

It is conceivable that few actual objects include two or more areas in which the reflection spectrums do not overlap one another at all as described above, but as a closely analogous example, the example is cited, in which in dental observation, irradiation of a band of a blue color system is performed to observe a tooth taking on a yellow tinge in a color closer to a white color, and irradiation of a band of a red color system is performed to observe a gingiva portion in a healthier color. The case can be considered with the reflection spectrum of the tooth being made to correspond to the aforementioned reflection spectrum r1, the light of the band of the blue color system with which the tooth is irradiated being made to correspond to the light of the aforementioned light emission spectrum 11, the reflection spectrum of the gingiva being made to correspond to the aforementioned reflection spectrum r2, and the light of the band of the red color system with which the gingiva is irradiated being made to correspond to the light of the aforementioned light emission spectrum 12, respectively.

In the present embodiment, the light of each of the irradiation modes is configured by the combination of the light emitted by the light emitting element, and the light of the phosphor (namely, the phosphor as a wavelength converting section which performs wavelength conversion) which is excited by the light and performs fluorescence emission. More specifically, in the first irradiation mode, irradiation of the first specific band is performed by the light of the first light emitting element, and irradiation of the second specific band is performed by the light of the fluorescence emission of the first phosphor (this is because the excitation band of the phosphor has a shorter wavelength than the fluorescence emission band, and it is inevitable that the first specific band becomes the emission band of the light emitting element which emits an excitation light and the second specific band becomes the band of fluorescence emission by the phosphor).

The light emission band indicates the band having an intensity not less than a predetermined ratio (for example, a half value) of the light emission intensity peak. Further, the excitation band indicates the band having an intensity of not less than a predetermined ratio (for example, a half value) of the excitation intensity peak. Furthermore, the fluorescence emission band indicates the band having an intensity of not less than a predetermined ratio of the fluorescence emission intensity peak (for example, a half value). Here, the predetermined ratio relating to the light emission band, the predetermined ratio relating to the excitation band, and the predetermined ratio relating to the fluorescence emission band may be values different from one another, as a matter of course.

Further, in the second irradiation mode, irradiation of the second irradiation band which is used in the second irradiation mode is performed by the combination of the light of the second light emitting element and the light of the second phosphor. This is because in the case of use of, for example, a semiconductor light emitting element as a light emitting element to realize reduction in size and weight, the light emission band of the semiconductor light emitting element is narrow, and therefore, the phosphor is also used in combination to supplement the band. More specifically, it is difficult to realize, for example, white color irradiation with an only single light emitting element, but by combination of a phosphor, white color irradiation can be substantially realized. However, in the second irradiation mode, irradiation of lights of a third and a fourth specific bands which are different from the aforementioned first and second specific bands may be performed as described above. In the case, if the fourth specific band has a longer wavelength than the third specific band, irradiation of the third specific band is performed by the light of the second light emitting element, and irradiation of the fourth specific band is performed by the light of the fluorescence emission of the second phosphor.

Figure 1:
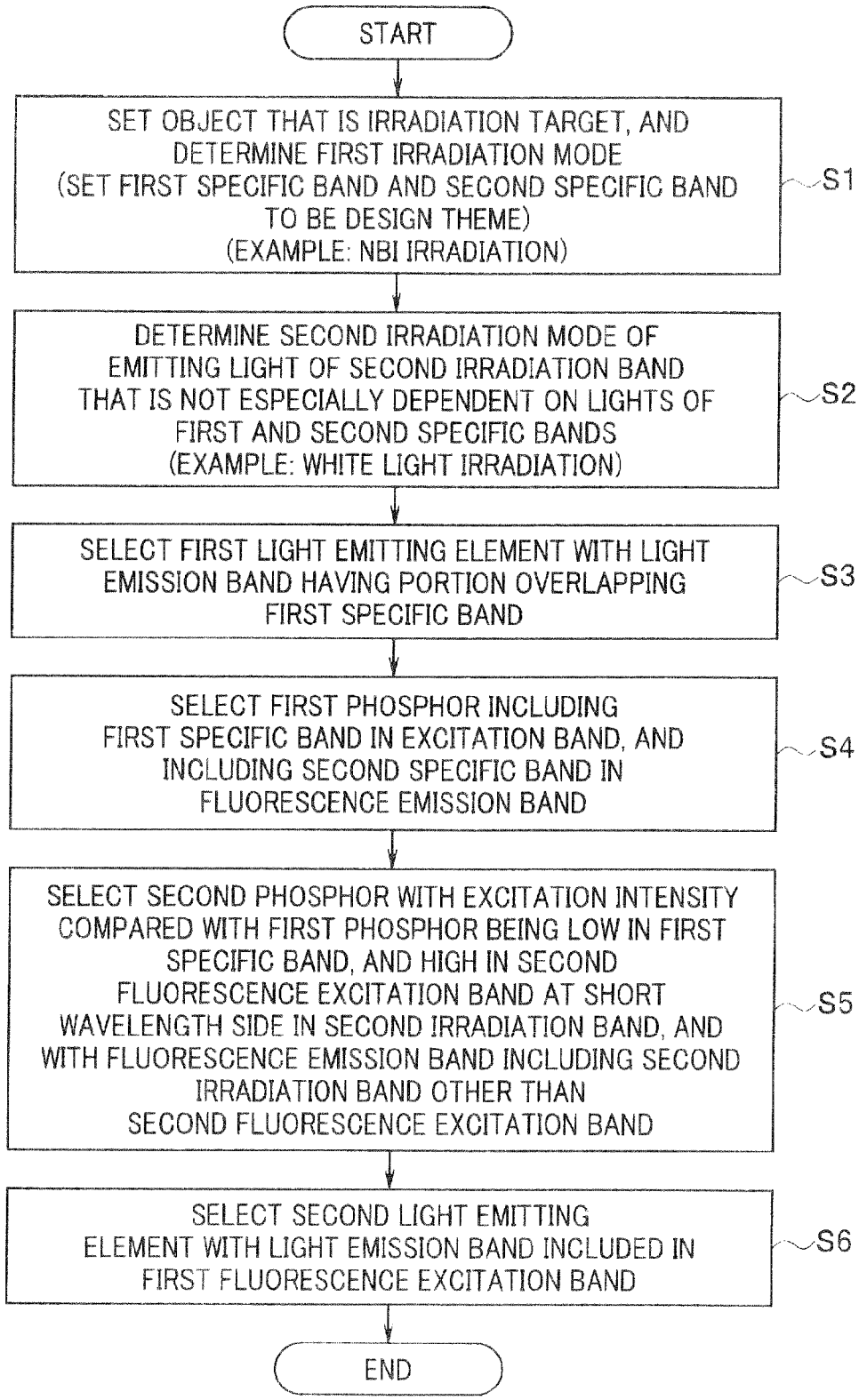
FIG. 1 is a flowchart showing a procedure of determining a first and a second light emitting elements and a first and a second phosphors in accordance with an object to be an irradiation target, in embodiment 1 of the present invention.

Here, FIG. 1 is a flowchart showing a procedure of determining the first and the second light emitting elements and the first and the second phosphors in accordance with the object to be an irradiation target.

First, when a light emitting apparatus is designed, an object which is a target for performing irradiation by the light emitting apparatus is set. Subsequently, in accordance with the object, the first specific band and the second specific band in the first irradiation mode are set (as described above, it is assumed that the wavelength of the first specific band<the wavelength of the second specific band) (step S1).

Next, in accordance with what observation is desired to be performed for the object, the second irradiation mode of emitting the light of the second irradiation band differing in the spectrum distribution of the light from the first irradiation mode (more specifically, not especially dependent on the lights of the first and the second specific bands) is set (step S2).

Subsequently, as the first light emitting element, the light emitting element which emits the light of the wavelength included in the first specific band (does not have to be of a wide band which covers all of the first specific band, and may be a bright line spectrum if only included in the first specific band), more specifically, the light emitting element with the light emission band having a portion which overlaps the first specific band is selected (step S3).

Further, as the first phosphor, the phosphor which includes the first specific band in the excitation band, and includes the second specific band in the fluorescence emission band is selected (step S4).

Next, as the second phosphor, the phosphor which satisfies the conditions (A) to (C) as follows is selected (step S5).

(A) The phosphor the excitation intensity of which is lower than the excitation intensity of the first phosphor in the first specific band (the excitation intensity of the second phosphor is not more than a predetermined ratio which is smaller than one (for example, not more than 9/10, more desirably not more than a half) of the excitation intensity of the first phosphor in the first specific band).

(B) The phosphor the excitation intensity of which is higher than the excitation intensity of the first phosphor in the excitation band (described as the second fluorescence excitation band) at a short wavelength side in the second irradiation band (the excitation intensity of the second phosphor is not less than a predetermined multiple larger than one (for example, not less than 10/9, more desirably twice or more) of the excitation intensity of the first phosphor) in the second fluorescence excitation band.

(C) The fluorescence emission band includes the second irradiation band other than the second fluorescence excitation band.

Here, the condition (A) means that the phosphor does not perform fluorescence emission so intensely as the first phosphor even when the phosphor receives the light of the first light emitting element. Accordingly, the contrast of the image which is acquired in the first irradiation mode (an example: NBI irradiation) is not reduced so much.

The condition (B) means that the phosphor performs fluorescence emission more intensely than the first phosphor when the phosphor receives the light of the second light emitting element. Accordingly, the first phosphor does not play a dominant role in the second irradiation mode (an example: white color irradiation).

The condition (C) means that when the light of the second light emitting element and the fluorescence emission of the second phosphor are combined, the light (an example: white color light) which is used in the second irradiation mode is configured. The second irradiation band is not limited to the irradiation band which is configured by one continuous band, but may be configured by a plurality of separated bands (example 1: the case in which the light emission band of the second light emitting element and the fluorescence emission band of the second phosphor are separated, example 2: the case in which a white color light is configured by lights with three peaks having peaks respectively at R, G and B, and the like).

Further, on the occasion of selection of the second phosphor, it is further desirable to select (D) such a second phosphor that the excitation band of the second phosphor does not overlap the fluorescence emission band of the first phosphor. The condition (D) is for preventing the second phosphor from performing fluorescence emission by the fluorescence emission from the first phosphor exciting the second phosphor as much as possible in the first irradiation mode. More specifically, if the condition (D) is satisfied, loss of the fluorescence emission light from the first phosphor in the first irradiation mode can be prevented, and reduction of the contrast of the image by the fluorescence emission of the second phosphor can be prevented.

In addition, on the occasion of selection of the second phosphor, (E) it is further desirable to select such a second phosphor that the fluorescence emission band of the second phosphor does not overlap the excitation band of the first phosphor. The condition (E) is for preventing the first phosphor from performing fluorescence emission by the fluorescence emission from the second phosphor exciting the first phosphor as much as possible in the second irradiation mode. More specifically, if the condition (E) is satisfied, loss of the fluorescence emission light from the second phosphor in the second irradiation mode can be prevented.

Subsequently, as the second light emitting element, the light emitting element the light emission band of which is included in the second fluorescence excitation band is selected (step S6). This means that the second light emitting element bears the short wavelength band in the second irradiation mode, and the second phosphor is caused to perform fluorescence emission more intensely than the first phosphor, as described above.

The flow shown in FIG. 1 shows one example, and is not limited to the sequence. For example, the processing of step S1 needs to be performed before the processing of step S3 and step S4, but it is sufficient that the processing of step S2 is performed before the processing of step S5 and step S6. Accordingly, it is also possible to perform the processing of step S2 of FIG. 1 after the processing of step S4 of FIG. 1 is performed.

Figure 2:
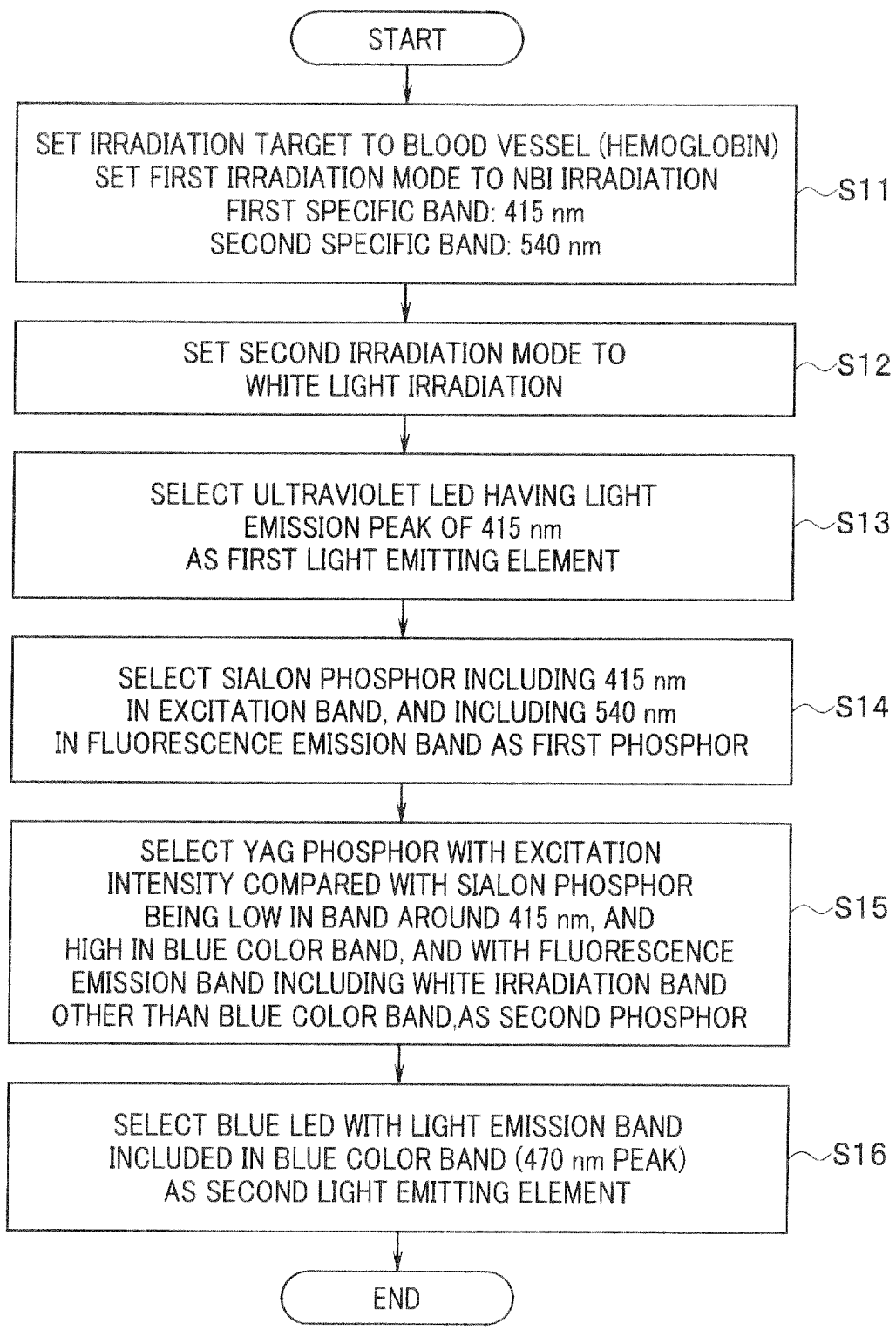
FIG. 2 is a flowchart showing a procedure of determining the first and the second light emitting elements and the first and the second phosphors when the object is set to a body tissue including a blood vessel (hemoglobin), in the above described embodiment 1.
Figure 16:
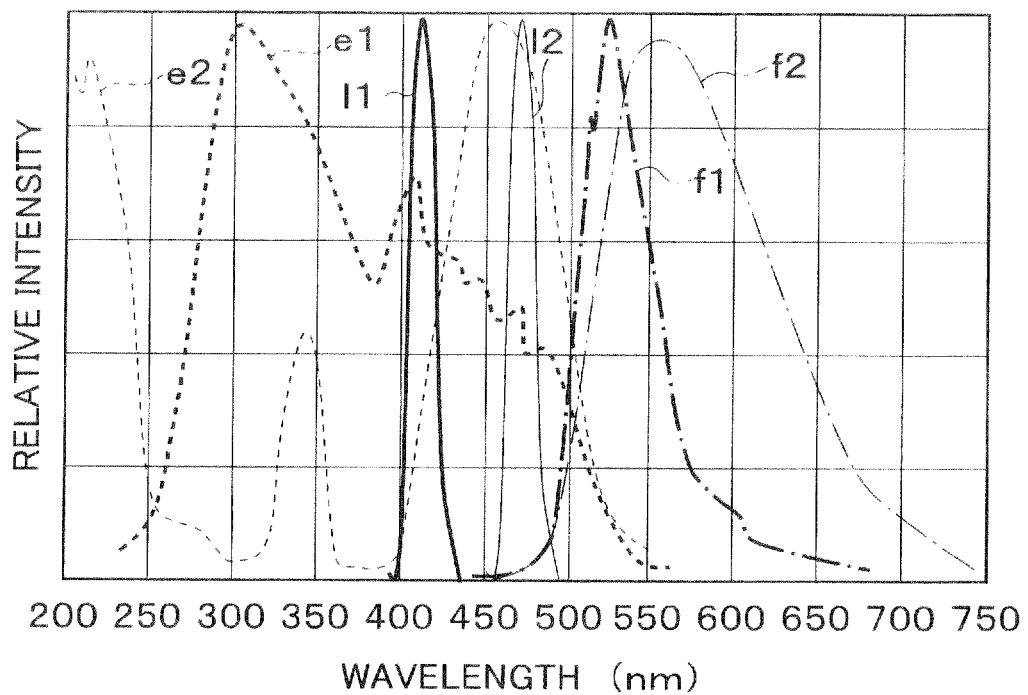
FIG. 16 is a diagram showing light emission spectrums of the first and the second light emitting elements, and excitation spectrums and fluorescence spectrums of the first and the second phosphors, in the above described embodiment 1.

Next, with reference to FIG. 2 and FIG. 16, the flow of the processing shown in FIG. 1 in the case of performing NBI irradiation as the first irradiation mode, and performing white color irradiation as the second irradiation mode will be described specifically. Here, FIG. 2 is a flowchart showing a procedure of determining the first and the second light emitting elements and the first and the second phosphors when the object is set to a body tissue including a blood vessel (hemoglobin). Further, FIG. 16 is a diagram showing light emission spectrums of the first and the second light emitting elements, and the excitation spectrums and the fluorescence spectrums of the first and the second phosphors. In FIG. 16, the axis of abscissa is common, but the axes of ordinates have relative scales of respective kinds of spectrums.

When the processing is started, the irradiation target is set to a body tissue including a blood vessel (hemoglobin) first, and the first irradiation mode is set to NBI irradiation (step S11). Thereby, as described above, the first specific band is determined to be a narrow band around 415 nm, and the second specific band is determined to be a narrow band around 540 nm.

Next, in order to enable normal light imaging of the body tissue, the second irradiation mode is determined to be white color light irradiation (step S12).

Subsequently, as the first light emitting element, an ultraviolet LED (semiconductor light emitting element) which performs narrow band light emission having the peak of the light emission intensity in the vicinity of a wavelength of 415 nm is selected so that the light emission band has a portion which overlaps the first specific band (see a light emission spectrum 11 of FIG. 16) (step S13).

Further, as the first phosphor, a SiAlON phosphor which includes 415 nm in the excitation band (see an excitation spectrum e1 of FIG. 16), and includes 540 nm in the fluorescence emission band (more specifically, has the peak of the fluorescence emission intensity in the vicinity of a wavelength of 540 nm) (see a fluorescence emission spectrum f1 of FIG. 16) (step S14).

Subsequently, as the second phosphor, a YAG phosphor with the excitation intensity as compared with a SiAlON phosphor being low in the band around 415 nm, and high in a blue color band (band at a short wavelength side in the second irradiation band, and, for example, a band of 450 to 485 nm) (see an excitation emission spectrum e2 of FIG. 16), and with the fluorescence emission band including a white color irradiation band (for example, a band of 520 to 630 nm (band including a green color light and a red color light)) other than the blue color band (see a fluorescence emission spectrum f2 of FIG. 16) is selected (step S15).

Thereafter, as the second light emitting element, a blue color LED which is a semiconductor light emitting element with a light emission band included in the blue color band in which the excitation intensity of the aforementioned YAG phosphor is higher than the excitation intensity of the SiAlON phosphor is selected (see a light emission spectrum 12 of FIG. 16) (step S16), and the processing ends. In the case, the blue color LED preferably has the peak of the light emission intensity in the vicinity of the wavelength to be the peak of the excitation spectrum of the YAG phosphor. In the present embodiment, the peak of the light emission intensity of the blue color LED is set at 470 nm. Here, the light emitted by the blue color LED which is the second light emitting element becomes a complementary color of the light which is fluorescently emitted by the YAG phosphor which is the second phosphor.

The first irradiation mode is set to be NBI irradiation, the phosphor with the fluorescence emission band as narrow as possible (with narrow band fluorescence emission) is desirably selected as the first phosphor. Thus, the SiAlON phosphor with the fluorescence emission band being a narrower band as compared with the YAG phosphor which is the second phosphor is selected as the first phosphor. Thereby, the light which is not included in the second specific band is prevented from being fluorescently emitted as much as possible, and the contrast of the blood vessel image is prevented from being reduced.

Figure 8:
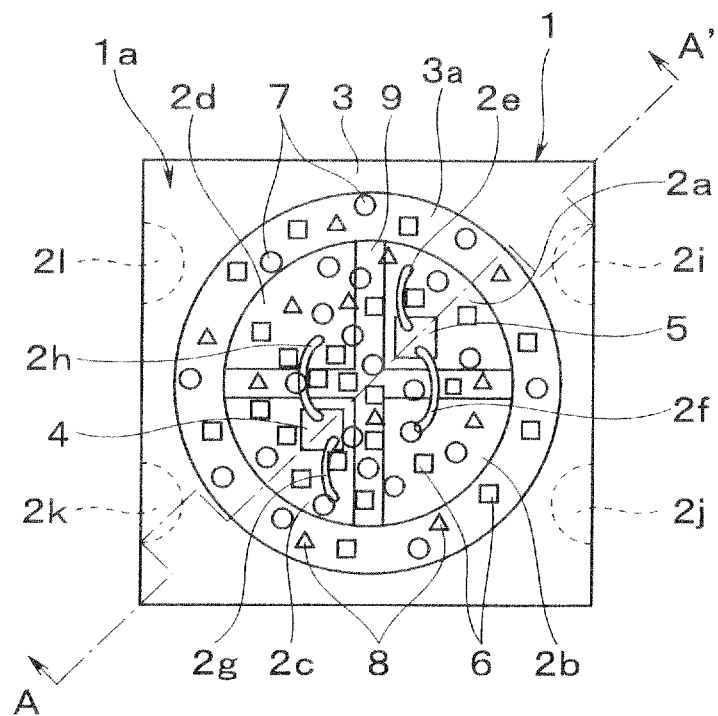
FIG. 8 is a plan view showing a structure of a light source apparatus in the above described embodiment 1.
Figure 9:
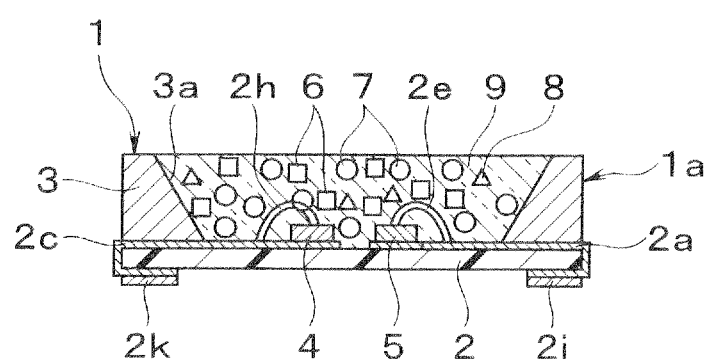
FIG. 9 is a sectional view taken along the A-A' of FIG. 8 which shows the structure of the light source apparatus in the above described embodiment 1.

Next, with reference to FIG. 8 and FIG. 9, a structure of the light source apparatus which is configured with use of the light emitting elements and the phosphors which are selected as described above will be described. FIG. 8 is a plan view showing the structure of the light source apparatus, and FIG. 9 is a sectional view taken along A-A' of FIG. 8 showing the structure of the light source apparatus.

The light source apparatus 1 includes a casing 1a which opens toward an irradiation direction of a light, a first light emitting element 4, a second light emitting element 5, a first phosphor 6 and a second phosphor 7 which are provided in the casing 1a and selected as described above. The light source apparatus 1 may further include a scatterer 8 in an inner portion of the casing 1a.

The casing 1a includes a printed board 2, and a cylindrical reflector 3 with a bottom surface side attached onto the printed board 2 and a top surface side to be an opening toward the irradiating direction of a light.

On a top surface of the printed board 2, a conductive pattern 2a forming a first cathode, a conductive pattern 2b forming a first anode, a conductive pattern 2c forming a second cathode, and a conductive pattern 2d forming a second anode are formed.

Meanwhile, on an undersurface of the printed board 2, electrodes 2i, 2j, 2k and 2l are formed, the conductive pattern 2a is electrically connected to the electrode 2i, the conductive pattern 2b is electrically connected to the electrode 2j, the conductive pattern 2c is electrically connected to the electrode 2k, and the conductive pattern 2d is electrically connected to the electrode 2l, respectively.

At positions to be an inner portion of the reflector 3 on the printed board 2, the first light emitting element 4 and the second light emitting element 5 which are selected as described above are mounted. More specifically, the second light emitting element 5 is placed on the conductive pattern 2a, is connected to the conductive pattern 2a via a gold wire 2e, and is connected to the conductive pattern 2b via a gold wire 2f. Further, the first light emitting element 4 is placed on the conductive pattern 2c, is connected to the conductive pattern 2c via a gold wire 2g, and is connected to the conductive pattern 2d via a gold wire 2h.

Further, the first phosphor 6 and the second phosphor 7 are configured as powder phosphors in the present embodiment. The first phosphor 6 and the second phosphor 7 are sealed in a recessed portion configured by the printed board 2 and the reflector 3 in a diffused state with use of a transparent resin 9, together with the scatterer 8 which is similarly formed as powder. More specifically, the first phosphor 6 and the second phosphor 7 are disposed at positions spatially overlapping each other. Thereby, the first light emitting element 4 and the second light emitting element 5 are in a state covered with the first phosphor 6, the second phosphor 7 and the scatterer 8. Both lights of the first light emitting element 4 and the second light emitting element 5 can reach the first phosphor 6, and both of the lights of the first light emitting element 4 and the second light emitting element 5 can reach the second phosphor 7.

In more detail, the first phosphors 6 are powder phosphors which are placed with such a density as to use a part of the light emitted by the first light emitting element 4 as the excitation light, and to cause another part of the light emitted by the first light emitting element 4 and at least a part of the light emitted by the second light emitting element 5 to scatter without being used as the excitation light. Similarly, the second phosphors 7 are powder phosphors which are placed with such a density as to use a part of the light emitted by the second light emitting element 5 as the excitation light, and to cause another part of the light emitted by the second light emitting element 5 and at least a part of the light emitted by the first light emitting element 4 to scatter without being used as the excitation light.

Further, the reflector 3 has an inner surface 3a formed into a taper shape (for example, a conical surface shape) which becomes larger in diameter toward the irradiating direction of the light, and can efficiently irradiate the emitted light toward the object.

Figure 10:
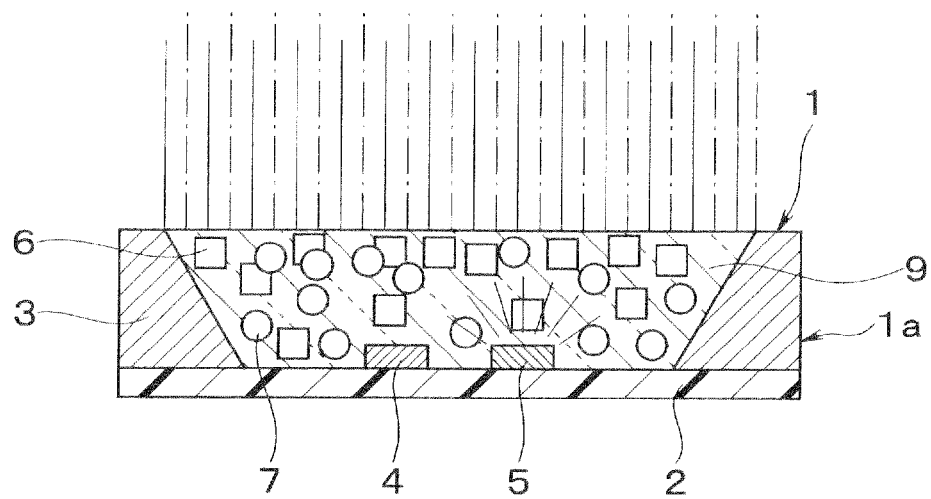
FIG. 10 is a view showing a state of the light source apparatus when the second light emitting element is caused to emit a light, in the above described embodiment 1.
Figure 11:
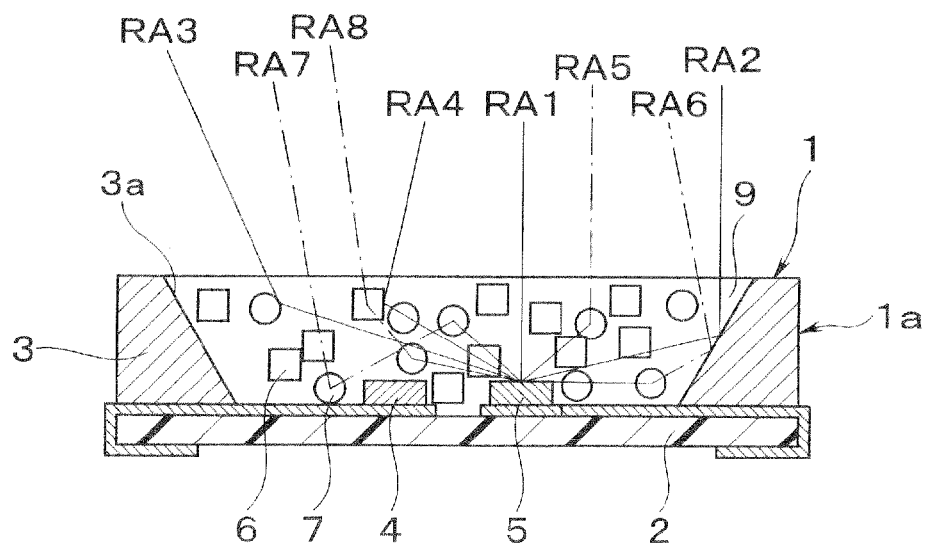
FIG. 11 is a view showing a state of a scattering of the light emitted from the second light emitting element, in the above described embodiment 1.
Figure 12:
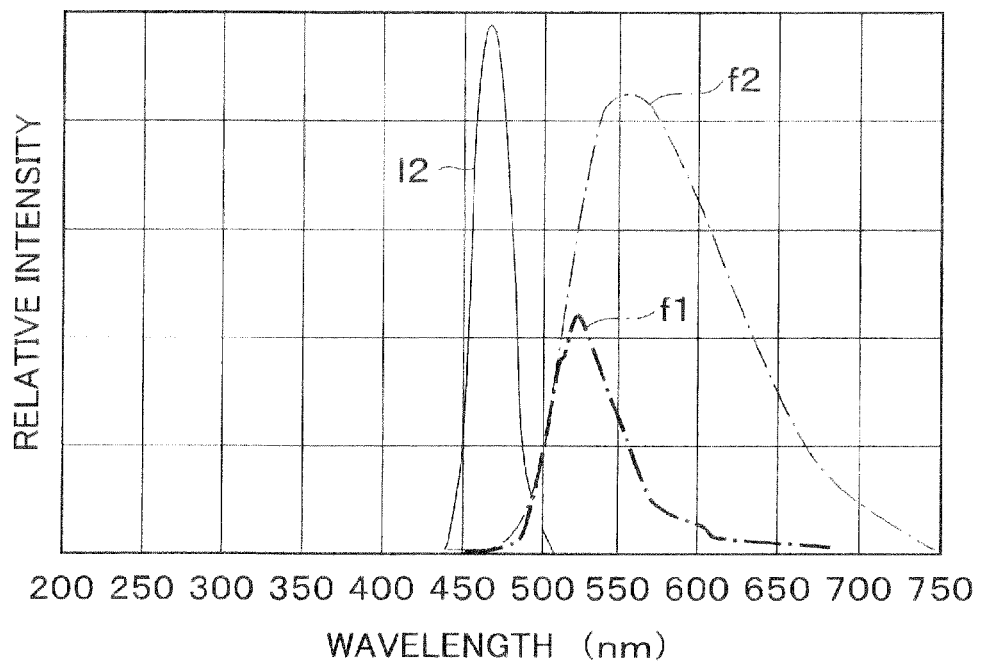
FIG. 12 is a diagram showing distributions of a light emission spectrum and a fluorescence spectrum when the second light emitting element is caused to emit a light, in the above described embodiment 1.

Next, a state in which the second light emitting element 5 is caused to emit a light in the light source apparatus 1 of the configuration as above will be described with reference to FIG. 10 to FIG. 12. FIG. 10 is a view showing a state of the light source apparatus 1 at the time of causing the second light emitting element 5 to emit a light, FIG. 11 is a view showing a state of a scattering of the light emitted from the second light emitting element 5, and FIG. 12 is a diagram showing distributions of the light emission spectrum and the fluorescence spectrum when the second light emitting element 5 is caused to emit a light. FIG. 10, FIG. 11, and FIG. 13 and FIG. 14 which will be described later show examples in the case without using the scatterer 8. One reason why the scatterer 8 is not used here is for simplifying the description and illustration, and another reason is that if diffusion of the light is sufficiently performed by the second phosphors 7 and the first phosphors 6 which are configured as powder phosphors, the necessary performance can be satisfied without use of the scatterer 8.

In the second irradiation mode, only the second light emitting element 5 is configured to emit a light as shown in FIG. 10. In the lights which are emitted by the second light emitting element 5 and radiated outside, a light which is directly radiated outside via the transparent resin 9, a light which is irradiated after being reflected or scattered by the first phosphors 6, the second phosphors 7 and the reflector 3, and a light which is irradiated directly or after being reflected or scattered after used as the excitation light of the first phosphors 6 and the second phosphors 7 and subjected to wavelength conversion are present.

Here, FIG. 11 shows states of light beams with the number of reflection times until being irradiated outside being zero or one in the second irradiation mode as RA1 to RA8.

(RA1) an emission light of the second light emitting element 5

(RA2) an emission light of the second light emitting element 5 reflected by the reflector 3

(RA3) an emission light of the second light emitting element 5 reflected by the second phosphor 7

(RA4) an emission light of the second light emitting element 5 reflected by the first phosphor 6

(RA5) a fluorescence emission light of the second phosphor 7

(RA6) a fluorescence emission light by the second phosphor 7 reflected by the reflector 3

(RA7) a fluorescence emission light by the second phosphor 7 reflected by the second phosphor 7

(RA8) a fluorescence emission light by the second phosphor 7 reflected by the first phosphor 6

Among the respective light beams shown in FIG. 11, RA3 can be ignored because the intensity of the reflection light becomes small when the excitation probability of the second phosphor 7 which receives the light emitted from the second light emitting element 5 is high. Further, the first phosphor 6 which receives the light emitted from the second light emitting element 5 slightly performs fluorescence emission, but is ignored here.

In an actual product, reflection/scattering is performed a larger number of times, and therefore, the light irradiated from the light source apparatus 1 becomes the light in which the emission light of the second light emitting element 5 and the fluorescence emission light by the second phosphor 7 are sufficiently mixed.

Further, the light emission spectrum and the fluorescence spectrum when the second light emitting element 5 is caused to emit a light are as shown in FIG. 12.

The shapes of the curves showing the respective spectrums are similar to the shapes shown in FIG. 16 described above, but the relative intensities are different. More specifically, in the light emission band shown by the light emission spectrum 12 of the second light emitting element 5, the excitation intensity of the second phosphor 7 is higher than the excitation intensity of the first phosphor 6 as shown in FIG. 16 (for example, higher by two-fold or more depending on the wavelength). Accordingly, the intensity of the fluorescence spectrum f2 of the second phosphor 7 is higher than the intensity of the fluorescence spectrum f1 of the first phosphor 6 (for example, higher by two-fold or more).

Figure 13:
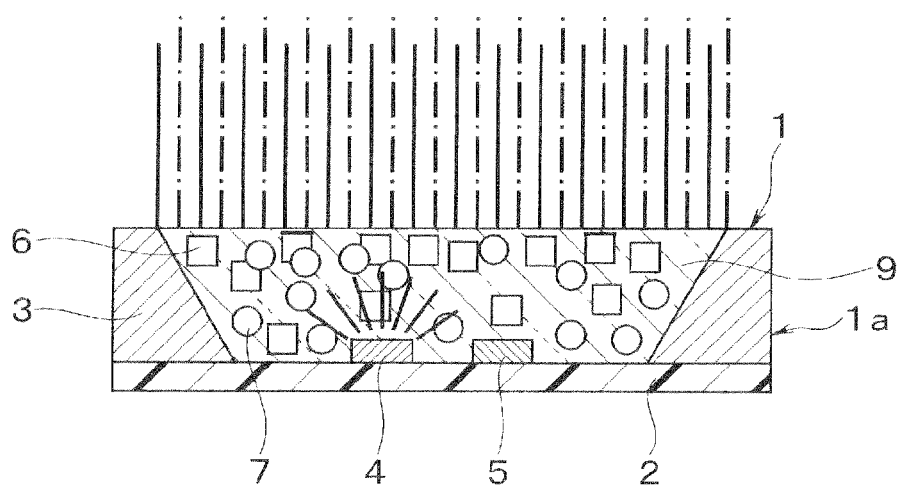
FIG. 13 is a view showing a state of the light source apparatus when the first light emitting element is caused to emit a light in the above described embodiment 1.

Subsequently, a state in which the first light emitting element 4 is caused to emit a light in the light source apparatus 1 will be described with reference to FIG. 13 to FIG. 15. FIG. 13 is a view showing a state of the light source apparatus 1 at the time of causing the first light emitting element 4 to emit a light, FIG. 14 is a view showing a state of a scattering of the light emitted from the first light emitting element 4, and FIG. 15 is a diagram showing distributions of the light emission spectrum and the fluorescence spectrum when the first light emitting element 4 is caused to emit a light.

In the first irradiation mode, only the first light emitting element 4 is configured to emit a light as shown in FIG. 13. In the lights which are emitted by the first light emitting element 4 and radiated outside, a light which is directly radiated outside via the transparent resin 9, a light which is irradiated after being reflected or scattered by the first phosphors 6, the second phosphors 7 and the reflector 3, and a light which is irradiated directly or after being reflected or scattered after used as the excitation light of the first phosphors 6 and the second phosphors 7 and subjected to wavelength conversion are present.

Figure 14:
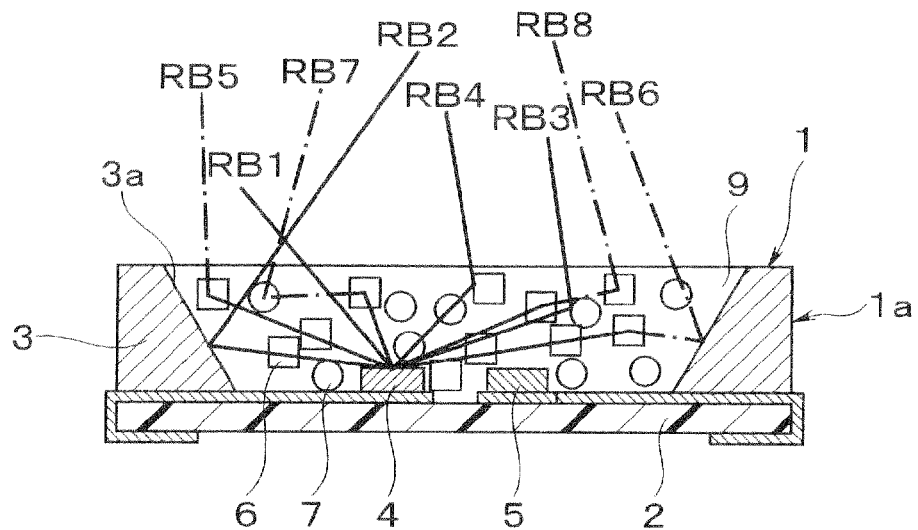
FIG. 14 is a view showing a state of a scattering of the light emitted from the first light emitting element, in the above described embodiment 1.
Figure 15:
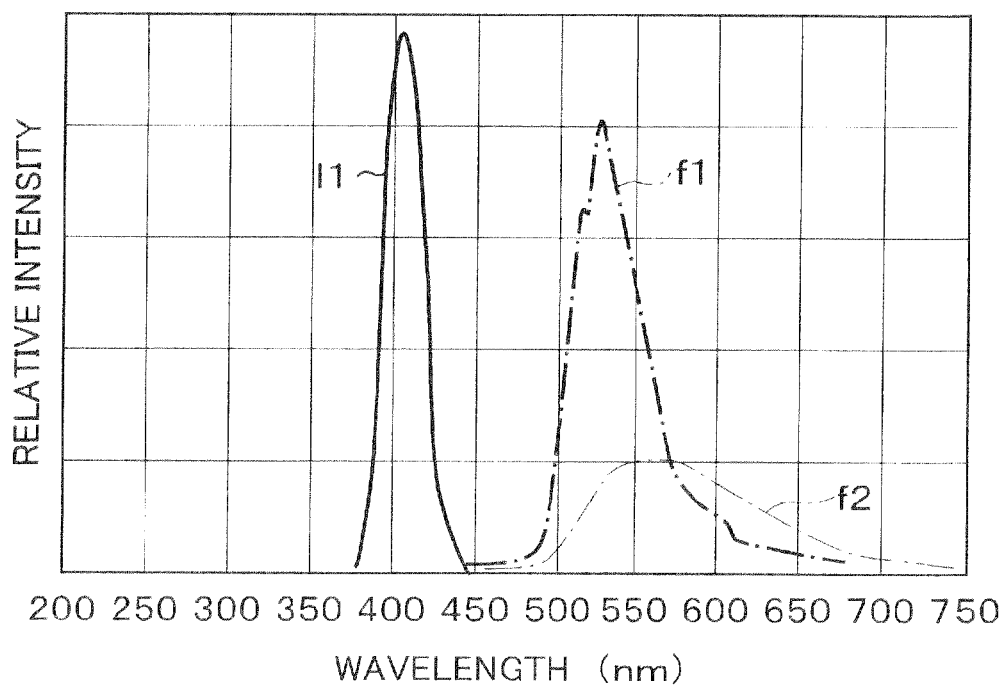
FIG. 15 is a diagram showing distributions of a light emission spectrum and a fluorescence spectrum when the first light emitting element is caused to emit a light, in the above described embodiment 1.

Here, FIG. 14 shows states of light beams with the number of reflection times until being irradiated outside being zero or one in the first irradiation mode as RB1 to RB8.

(RB1) an emission light of the first light emitting element 4

(RB2) an emission light of the first light emitting element 4 reflected by the reflector 3

(RB3) an emission light of the first light emitting element 4 reflected by the second phosphor 7

(RB4) an emission light of the first light emitting element 4 reflected by the first phosphor 6

(RB5) a fluorescence emission light of the first phosphor 6

(RB6) a fluorescence emission light by the first phosphor 6 reflected by the reflector 3

(RB7) a fluorescence emission light by the first phosphor 6 reflected by the second phosphor 7

(RB8) a fluorescence emission light by the first phosphor 6 reflected by the first phosphor 6

Among the respective light beams shown in FIG. 14, RB4 can be ignored because the intensity of the reflection light becomes small when the excitation probability of the first phosphor 6 which receives the light emitted from the first light emitting element 4 is high. Further, the second phosphor 7 which receives the light emitted from the first light emitting element 4 slightly performs fluorescence emission, but is also ignored here.

In an actual product, reflection/scattering is performed a larger number of times, and therefore, the light irradiated from the light source apparatus 1 becomes the light in which the emission light of the first light emitting element 4 and the fluorescence emission light by the first phosphor 6 are sufficiently mixed.

Further, the light emission spectrum and the fluorescence spectrum when the first light emitting element 4 is caused to emit a light are as shown in FIG. 15.

The shapes of the curves showing the respective spectrums are similar to the shapes shown in FIG. 16 described above, but the relative intensities are different. More specifically, in the light emission band shown by the light emission spectrum 11 of the first light emitting element 4, the excitation intensity of the first phosphor 6 is higher than the excitation intensity of the second phosphor 7 as shown in FIG. 16 (for example, higher by two-fold or more depending on the wavelength). Accordingly, the intensity of the fluorescence spectrum f1 of the first phosphor 6 is higher than the intensity of the fluorescence spectrum f2 of the second phosphor 7 (for example, higher by two-fold or more). In particular, when the first irradiation mode is NBI irradiation, the lower the intensity of the fluorescence spectrum f2 of the second phosphor 7 which becomes the cause of reducing the contrast of an image, the better. In the example shown in FIG. 15, the fluorescence emission intensity of the second phosphor 7 (see f2 of FIG. 15) can be said as sufficiently lower than the fluorescence emission intensity of the first phosphor 6 (see f1 of FIG. 15).

As above, both of the light emitted from the light source apparatus 1 in the first irradiation mode and the light emitted from the light source apparatus 1 in the second irradiation mode become the lights sufficiently scattered at the portions where the respective phosphors are sealed with the resin. Therefore, even if the positions of the first light emitting element 4 and the second light emitting element 5 in the light source apparatus 1 are different from each other, the light emitted from the light source apparatus 1 in the first irradiation mode, and the light emitted from the light source apparatus 1 in the second irradiation mode are not irradiated with different directional characteristics, but become the lights with the same directional characteristics.

With how much density the phosphors are resin-sealed depends on the optical design, and therefore, there can be some cases in which only the phosphors are insufficient to scatter lights sufficiently. In such cases, the scatterers 8 may be further added as shown in FIG. 8 and FIG. 9.

Figure 17:
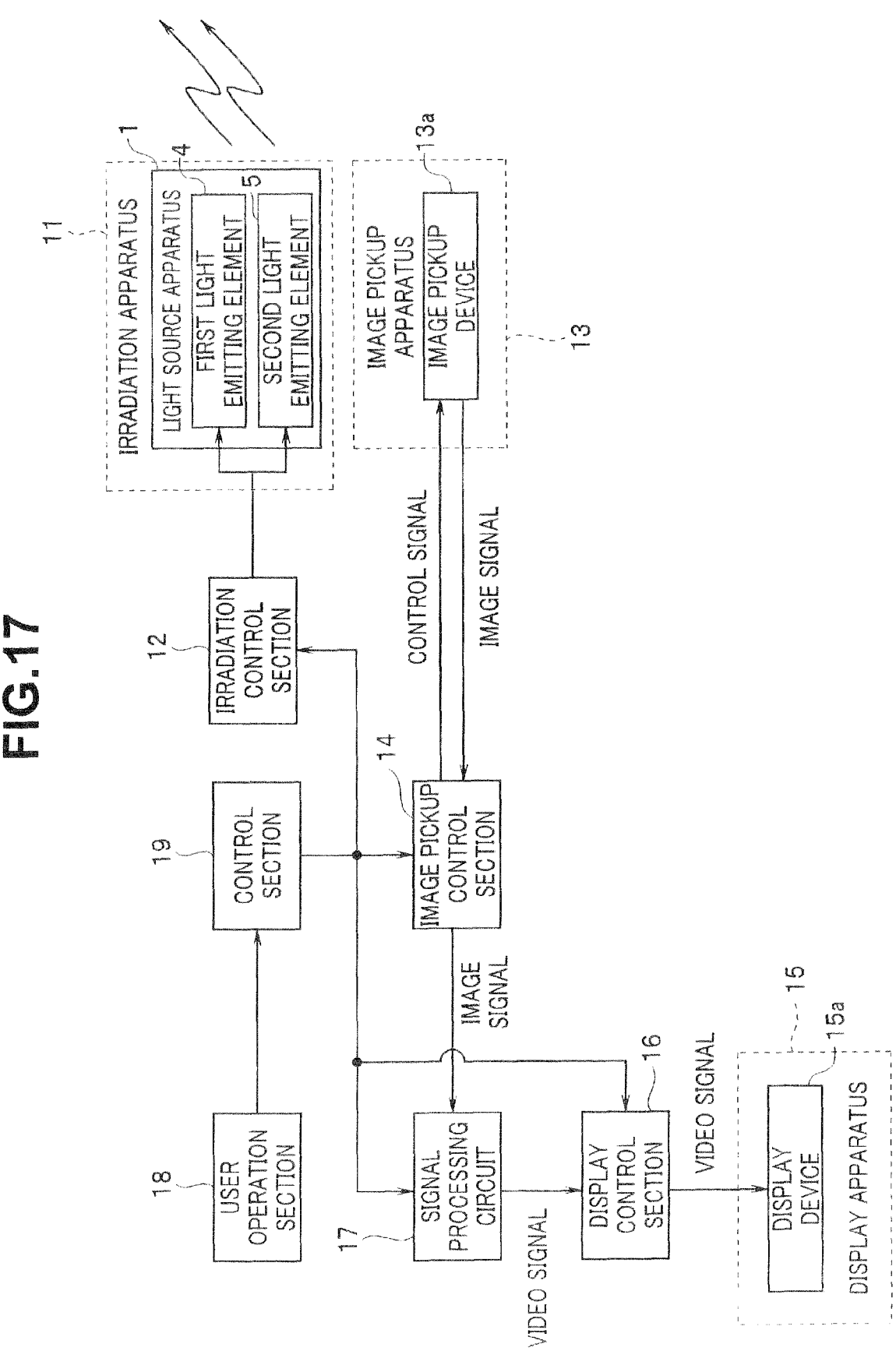
FIG. 17 is a block diagram showing a configuration of an electronic image acquiring apparatus including the light source apparatus of the above described embodiment 1.

Next, FIG. 17 is a block diagram showing a configuration of an electronic image acquiring apparatus including the light source apparatus 1.

The electronic image acquiring apparatus includes the light source apparatus 1 having the first light emitting element 4 and the second light emitting element 5 as described above, and an image pickup apparatus 13 having an image pickup device 13*a* that causes a light which is irradiated from the light source apparatus 1 and is reflected by the object to form an image by an optical system and picks up the image.

In more detail, the electronic image acquiring apparatus includes an irradiation apparatus 11 having the light source apparatus 1 described above, an irradiation control section 12, the image pickup apparatus 13 described above, an image pickup control section 14, a display apparatus 15, a display control section 16, a signal processing circuit 17, a user operation section 18, and a control section 19. The electronic image acquiring apparatus shown in FIG. 17 also includes the display apparatus 15 which displays an image picked up by the image pickup apparatus 13 as above, and therefore, also serves as an electronic image observation apparatus.

The irradiation apparatus 11 includes the light source apparatus 1 described above. As the irradiation apparatus 11, a configuration further including an irradiating optical system or the like in addition to the light source apparatus 1 can be cited as an example.

The irradiation control section 12 is for driving and controlling the irradiation apparatus 11, and controls the irradiation by the first irradiation mode and the irradiation by the second irradiation mode. For example, for the irradiation by the first irradiation mode and the irradiation by the second irradiation mode, control of alternately providing timing for the respective irradiations in a time division way, control of the light emission intensities of the first light emitting element 4 and the second light emitting element 5 in the respective irradiation modes and the like are performed.

The image pickup apparatus 13 includes the image pickup device 13*a*, and further includes the optical system for forming an optical image of an object on the image pickup device 13*a* and the like, as described above.

The image pickup control section 14 performs drive control by transmitting a control signal to the image pickup apparatus 13, and receives an image signal from the image pickup apparatus 13.

The display apparatus 15 is for displaying an image which is obtained by being irradiated by the irradiation apparatus 11 and picked up by the image pickup apparatus 13, and includes a display device 15*a*.

The display control section 16 performs control of causing the display apparatus 15 to perform display based on a video signal from the signal processing circuit 17.

The signal processing circuit 17 receives an image signal from the image pickup control section 14, performs image signal processing, generates a video signal for display and outputs the video signal to the display control section 16.

The user operation section 18 performs input of various operations to the electronic image acquiring apparatus. As the operations which can be inputted by the user operation section 18, an on/off operation of a power supply of the electronic image acquiring apparatus, a change operation of the first irradiation mode of causing the first light emitting element 4 to emit a light and the second irradiation mode of causing the second light emitting element 5 to emit a light, the image pickup operation of the image pickup apparatus 13 and the like are cited as some examples.

The control section 19 totally controls the respective sections in the electronic image acquiring apparatus including the irradiation control section 12, the image pickup control section 14, the display control section 16, the signal processing circuit 17 and the like by receiving the operation input from the user operation section 18.

When the first irradiation mode (for example, special observation by NBI irradiation) is selected by the user via the user operation section 18 in the configuration as above, the irradiation control section 12 causes only the first light emitting element 4 to emit a light based on the command of the control section 19. The light emitted from the first light emitting element 4 is partially subjected to wavelength conversion by the first phosphor 6 to be a fluorescent light. Thus, the object is irradiated with the narrow band light of the first specific band emitted by the first light emitting element 4 and the narrow band light of the second specific band fluorescently emitted by the first phosphor 6 as NBI irradiation lights.

Meanwhile, when the second irradiation mode (for example, normal observation by white color irradiation) is selected by a user via the user operation section 18, the irradiation control section 12 causes only the second light emitting element 5 to emit a light based on the command of the control section 19. The light emitted from the second light emitting element 5 is partially subjected to wavelength conversion by the second phosphor 7 to be a fluorescent light, and subjected to color mixing to be emitted to the object as a white color light.

Since the electronic image acquiring apparatus can optionally switch the first irradiation mode (for example, NBI irradiation) and the second irradiation mode (for example, white color irradiation) by the one light source apparatus 1 as above, the electronic image acquiring apparatus does not need to include a plurality of light source apparatuses corresponding to the irradiation modes, and can realize reduction in size, reduction in weight and reduction in cost.

Figure 18:
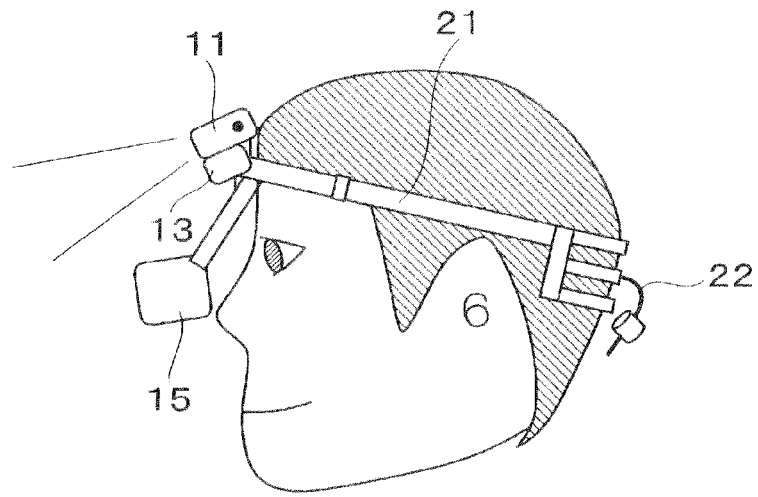
FIG. 18 is a side view showing a configuration of a head-mounted type electronic image observation apparatus in a mounted state, in the above described embodiment 1.
Figure 19:
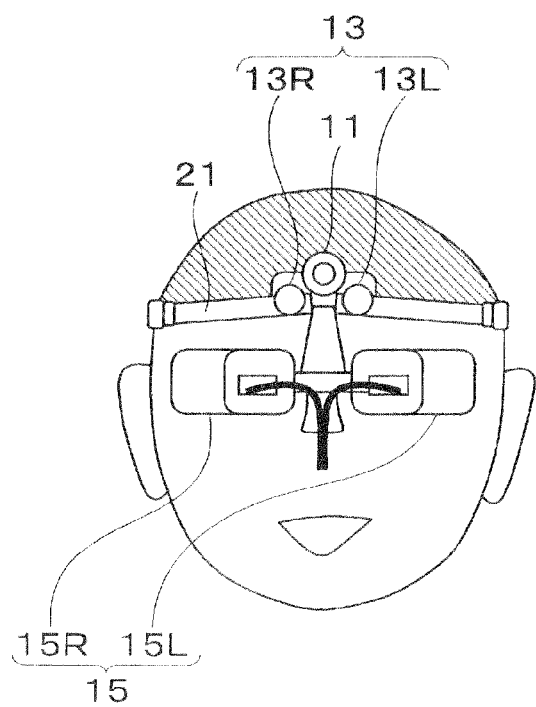
FIG. 19 is a front view showing the configuration of the head-mounted type electronic image observation apparatus in the mounted state, in the above described embodiment 1.

Subsequently, with reference to FIG. 18 and FIG. 19, a head-mounted type electronic image observation apparatus will be described. Here, FIG. 18 is a side view showing a configuration of the head-mounted type electronic image observation apparatus in a mounted state, and FIG. 19 is a front view showing the configuration of the head-mounted type electronic image observation apparatus in the mounted state.

The head-mounted type electronic image observation apparatus is the result of the electronic image observation apparatus (electronic image acquiring apparatus) as shown in FIG. 17 being configured into a form with which a user can use the electronic image observation apparatus by mounting the apparatus on a head portion (a so-called, head mount display (HMD)).

More specifically, the head-mounted type electronic image observation apparatus includes a frame portion 21 to be mounted on a head portion substantially similarly to eyeglasses. A fixing band 22 for preventing falling off of the frame portion 21 is attached to a position to be a rear head portion side of the user at the time of being mounted, of the frame portion 21.

Further, a pair of left and right image pickup apparatuses 13 (a left eye image pickup apparatus 13L and a right eye image pickup apparatus 13R) and the irradiation apparatus 11 including the light source apparatus 1 as described above are placed at a portion of the frame portion 21 which is located at a forehead front side of a user at the time of being mounted. Here, the left eye image pickup apparatus 13L and the right eye image pickup apparatus 13R are placed so that the respective image pickup optical axes intersect each other with predetermined angles of convergence. Meanwhile, the light source apparatus 1 is placed at a slightly upper side between the left eye image pickup apparatus 13L and the right eye image pickup apparatus 13R, for example.

Further, a pair of left and right display apparatuses 15 (a left eye display apparatus 15L and a right eye display apparatus 15R) are provided to hang from a portion of the frame portion 21 which is located at the forehead front side of the user at the time of being mounted. Here, the left eye display apparatus 15L is disposed so as to be located at a slightly lower side in front of a left eye of the user at the time of being mounted, whereas the right eye display apparatus 15R is disposed so as to be located at a slightly lower side in front of a right eye of the user at the time of being mounted respectively (see FIG. 18), and positional adjustment thereof can be performed.

The image which is picked up by the left eye image pickup apparatus 13L is displayed in the left eye display apparatus 15L, and the image which is picked up by the right eye image pickup apparatus 13R is displayed in the right eye display apparatus 15R. Accordingly, the user can three-dimensionally observe an object (performs stereopsis) by the display apparatus 15 if the user looks at a slightly lower side of the field of view. Meanwhile, if the user looks at a slightly upper side of the field of view, the user can take straight look from a space between the display apparatus 15 and the frame portion 21.

In the configuration as above, an operation at the time of irradiation by the irradiation apparatus 11 including the light source apparatus 1 is the same as described with reference to FIG. 17.

The head-mounted type electronic image observation apparatus is desired to be especially compact and light with high portability to reduce the burden on the user at the time of being mounted, and by including the light source apparatus 1 of the configuration as described above, reduction in size, simplification of the circuit configuration and reduction in cost can be realized.

Next, with reference to FIG. 20 and FIG. 21, an endoscope apparatus will be described. Here, FIG. 20 is a view showing a configuration of an endoscope system including the endoscope apparatus, and FIG. 21 is a sectional view showing a configuration of an insertion portion distal end portion of the endoscope apparatus.

Figure 20:
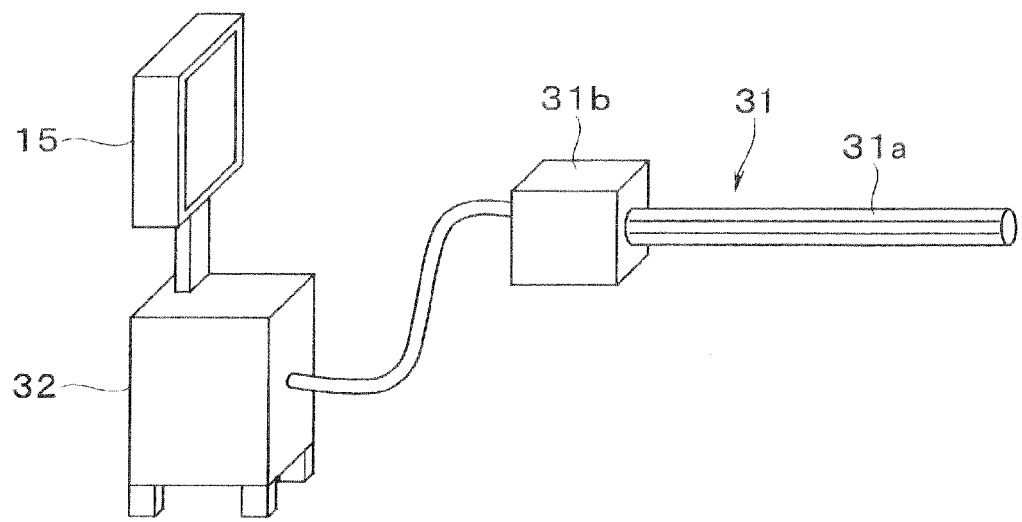
FIG. 20 is a view showing a configuration of an endoscope system including an endoscope apparatus, in the above described embodiment 1.
Figure 21:
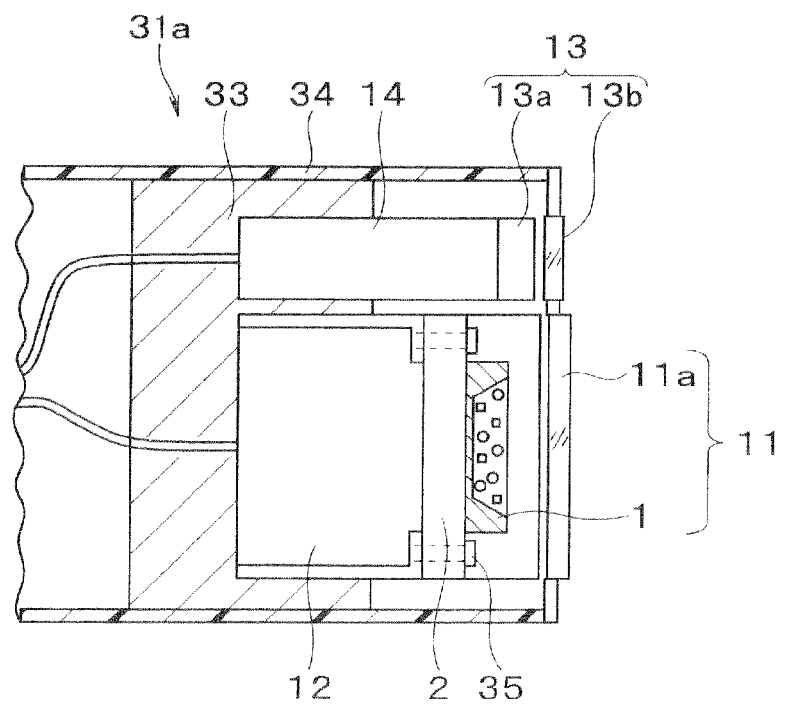
FIG. 21 is a sectional view showing a configuration of an insertion portion distal end portion of the endoscope apparatus, in the above described embodiment 1.

First, the endoscope system includes an endoscope apparatus 31, a camera control unit (CCU) 32 and the display apparatus 15, as shown in FIG. 20.

The endoscope apparatus 31 includes an elongated insertion portion 31a for being inserted into a body cavity of an object to be examined, and an operation section 31b which is for performing operation at a user's hand side and configures a part of the above described user operation section 18. The irradiation apparatus 11 including the light source apparatus 1 and the image pickup apparatus 13 are placed at a distal end side of the insertion portion 31a, as will be described later.

The CCU 32 is connected to the endoscope apparatus 31 and includes the display control section 16, the signal processing circuit 17, another part of the user operation section 18 and the control section 19 as described above.

The display apparatus 15 is connected to the CCU 32, and displays an image picked up by the endoscope apparatus 31 and other various kinds of information.

The irradiation apparatus 11 (including the light source apparatus 1) and the image pickup apparatus 13 which configure the electronic image acquiring apparatus as shown in FIG. 17 are disposed at a distal end portion of the insertion portion 31a of the endoscope apparatus 31. Further, an irradiating optical element 11a for irradiating an object with a light from the light source apparatus 1, and an observing optical element 13b which configures an optical system for forming an optical image of the object on the image pickup device 13a of the image pickup apparatus 13 are disposed on a distal end face in the distal end portion of the insertion portion 31a of the endoscope apparatus 31.

Here, the irradiation control section 12 performs the same irradiation control as the irradiation control section 12 in the electronic image acquiring apparatus as shown in FIG. 17. The image pickup device 13a of the image pickup apparatus 13 is mounted on the image pickup control section 14 which is configured as an image pickup board or the like. Further, the printed board 2 of the light source apparatus 1 is fixed and further electrically connected to the irradiation control section 12 configured as an irradiation board or the like via a fixing screw 35 or the like. The image pickup control section 14 and the irradiation control section 12 are fixed to a base portion 33 which configures a distal end rigid portion in the distal end portion of the insertion portion 31a, and are covered with an outer sheath 34.

The optical system for forming an optical image of the object on the image pickup device 13a does not have to be entirely placed at the distal end portion of the insertion portion 31a. For example, such a configuration may be adopted that only the observing optical element 13b which configures a part of the optical system is placed at the distal end portion of the insertion portion 31a, a fiber bundle or the like which transmits the optical image of the object which is formed by the observing optical element 13b to the user's hand side is placed inside the insertion portion 31a, and the image pickup device 13a which photoelectrically converts the transmitted optical image is placed in the operation section 31b or the like at the user's hand side of the endoscope apparatus 31. Accordingly, it is sufficient if only the observing optical element 13b which configures at least a part of the optical system of the image pickup apparatus 13 is disposed at the distal end portion of the insertion portion 31a of the endoscope apparatus 31.

Further, the light source apparatus 1 is disposed at the distal end portion of the insertion portion 31a of the endoscope apparatus 31 in the above description, but the light source apparatus 1 is not limited to the configuration. For example, such a configuration may be adopted that the light source apparatus 1 is placed in the operation section 31b or the CCU 32, and the light emitted from the light source apparatus 1 is guided to the distal end portion of the insertion portion 31a with use of an optical fiber or the like to perform irradiation.

In the configuration as above, the operation at the time of irradiation by the irradiation apparatus 11 including the light source apparatus 1 is the same as described with reference to FIG. 17.

In the endoscope apparatus, the insertion portion 31a is desired to have a small diameter, and when the light source apparatus 1 is especially disposed at the distal end portion of the insertion portion 31a, the light source apparatus 1 of the configuration as described above is included, whereby reduction in the diameter of the insertion portion 31a can be achieved. Further, as described above, simplification of the circuit configuration and cost reduction can be realized.

Figure 22:
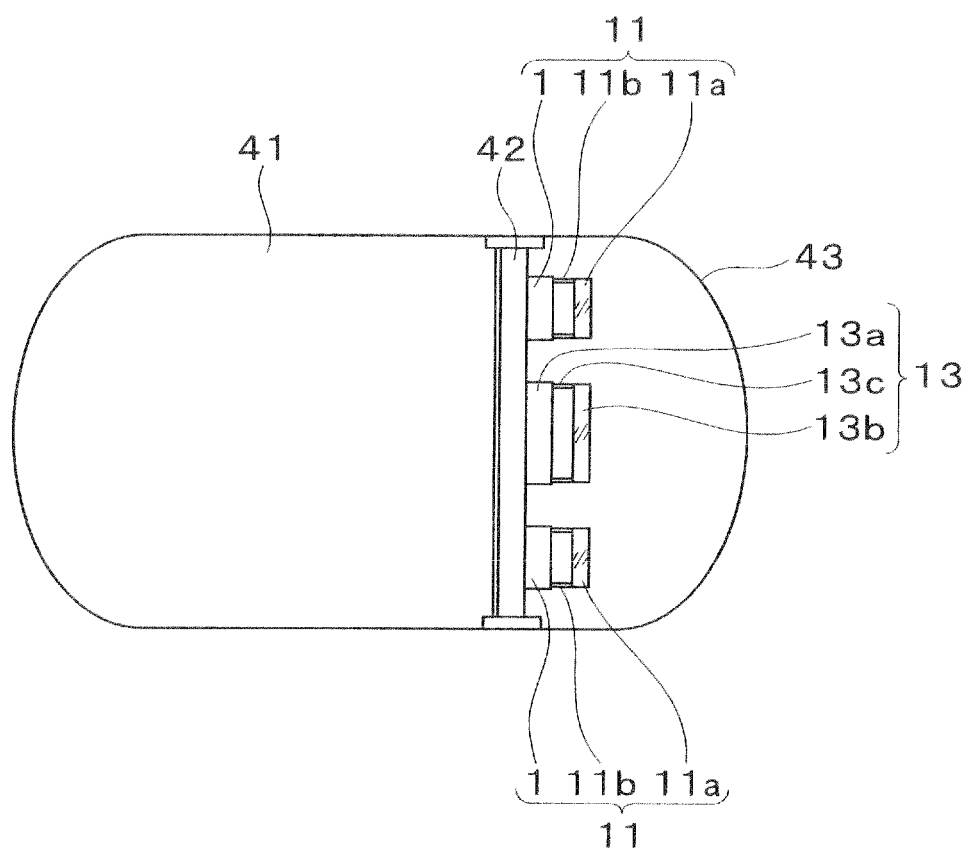
FIG. 22 is a side view showing a configuration of a capsule endoscope apparatus, in the above described embodiment 1.

Subsequently, FIG. 22 is a side view showing a configuration of a capsule endoscope apparatus.

The capsule endoscope apparatus houses the electronic image acquiring apparatus as shown in FIG. 17 having the irradiation apparatus 11 including the light source apparatus 1 and the image pickup apparatus 13 in a capsule casing.

More specifically, the capsule endoscope apparatus includes a capsule casing which forms an outer shape in a substantially cylindrical shape as a whole, and a front end face side and a rear end surface side of the capsule casing are formed so as to form substantially semispherical shapes. A semispherical portion at the front end side of the capsule casing is a transparent cover 43, and the other portion of the capsule casing is a casing 41.

A board 42 is provided on a front end face of the casing 41, and the image pickup device 13a is mounted on, for example, a substantially central portion on the board 42. The observing optical element 13b which is an optical system for forming an optical image of the object on the image pickup device 13a is attached to the image pickup device 13a via an optical element housing portion 13c. In the example shown in FIG. 22, the image pickup apparatus 13 is configured by including the image pickup device 13a, the observing optical element 13b and the optical element housing portion 13c.

Further, one light source apparatus 1 is mounted in each of, for example, two positions with the image pickup apparatus 13 therebetween on the board 42, that is, two in total are mounted. Irradiating optical elements 11a are respectively attached to the light source apparatuses 1 via the respective optical element housing portions 11b. In the example shown in FIG. 22, the irradiation apparatus 11 is configured by including the light source apparatus 1, the irradiating optical element 11a and the optical element housing portion 11b.

Further, the image pickup apparatus 13 and the irradiation apparatuses 11 are covered with the above described transparent cover 43.

Though not illustrated, the irradiation control section 12, the image pickup control section 14, the signal processing circuit 17 described above and the like are placed in the casing 41. Further, at least one of a memory for storing the video signals processed by the signal processing circuit 17 and a transmission section for transmitting the video signals by radio or the like is placed in the casing 41, though not illustrated.

In the configuration as above, an operation at the time of irradiation by the irradiation apparatus 11 including the light source apparatus 1 is substantially the same as described with reference with FIG. 17, but the irradiation by the first irradiation mode and the irradiation by the second irradiation mode are alternately performed in a time division way automatically. The image pickup apparatus 13 acquires the images in the respective irradiation modes in a time division way synchronously with change of the irradiation mode. The video signal which is thus acquired and processed by the signal processing circuit 17 is stored in the memory when the memory is included, is transmitted when the transmission section is included, and processing of both is performed when both of the memory and the transmission section are included.

In the above description, the two irradiation apparatuses 11 for symmetrically irradiating the object which is picked up by the image pickup apparatus 13 are provided at the positions with the image pickup apparatus 13 therebetween, but only one of the irradiation apparatuses 11 may be provided if it is sufficient for picking up the image of the object.

Further, in the above description, the first irradiation mode and the second irradiation mode are configured to be alternately performed automatically in a time-division way, but the first irradiation mode and the second irradiation mode are not limited to the configuration. For example, such a configuration may be adopted that a reception section not illustrated is provided in the casing 41, and a command from outside can be received by radio or the like. In such a case, the first irradiation mode and the second irradiation mode can be switched as desired by operation from outside.

The capsule endoscope apparatus is desired to be small in size, and the light source apparatus 1 of the configuration described above is included, whereby the reduction in size can be achieved. Furthermore, as described above, simplification of the circuit configuration and cost reduction can be achieved.

According to embodiment 1 as above, the light in the first irradiation mode, and the light in the second irradiation mode different in spectrum from the light in the first irradiation mode can be emitted in a time division way by one light source apparatus without being optically separated. Accordingly, the light source apparatus can be reduced in size, reduced in weight and reduced in cost. By extension, the electronic image acquiring apparatus, the electronic image observation apparatus, the endoscope apparatus, and the capsule endoscope apparatus which are configured with use of the light source apparatus as above can be reduced in size, reduced in weight and reduced in cost.

The present invention is not limited to the aforementioned embodiment as it is, but can be embodied with the components modified in the range without departing from the gist of the present invention in the practical stage. Further, by the proper combination of a plurality of components disclosed in the above described embodiment, various inventions can be formed. For example, several components may be deleted from all the components shown in the embodiment. Further, the components in different embodiments may be combined where appropriate. Various modifications and applications can be made within the range without departing from the gist of the invention as a matter of course.

What is claimed is:

1. A light source apparatus emitting a light of a first specific spectrum band and a light of a second specific spectrum band with a wavelength longer than the first specific spectrum band in a first irradiation mode, and emitting a light of a second irradiation band with a spectrum different from the light emitted in the first irradiation mode, in a second irradiation mode, the light source apparatus comprising:
   a casing that is opened toward an irradiating direction of the light;
   a first light emitting element that is provided in the casing, the first light emitting element emitting light in the first irradiation mode and not emitting the light in the second irradiation mode, and a light emission band of the first light emitting element having a portion that overlaps the first specific spectrum band;
   a first phosphor that is provided in the casing so that the light emitted by the first light emitting element can reach the first phosphor, the first phosphor including the first specific spectrum band in an excitation band thereof, and including the second specific spectrum band in a fluorescence emission band thereof;
   a second phosphor that is provided in the casing so that the light emitted by the first light emitting element reaches the second phosphor, an excitation intensity of the second phosphor, as compared with an excitation intensity of the first phosphor, being lower in the first specific spectrum band and higher in a second fluorescence excitation band at a short wavelength side in the second irradiation band, and a fluorescence emission band of the second phosphor including the second irradiation band other than the second fluorescence excitation band; and
   a second light emitting element that is provided in the casing so that light emitted from the second light emitting element can reach the first phosphor and the second phosphor, the second light emitting element emitting the light in the second irradiation mode and not emitting the light in the first irradiation mode, and a light emission band of the second light emitting element being included in the second fluorescence excitation band,
   wherein the first phosphor is a powder phosphor placed with such a density that the first phosphor uses a part of the light emitted by the first light emitting element as an excitation light, and scatters another part of the light emitted by the first light emitting element and at least a part of the light emitted by the second light emitting element without using the other part of the light emitted by the first light emitting element and at least a part of the light emitted by the second light emitting element as the excitation light, and
   the second phosphor is a powder phosphor that is placed with such a density that the second phosphor uses a part of the light emitted by the second light emitting element as an excitation light, and scatters another part of the light emitted by the second light emitting element and at least a part of the light emitted by the first light emitting element without using the other part of the light emitted by the second light emitting element and at least a part of the light emitted by the first light emitting element as the excitation light.

2. The light source apparatus according to claim 1, wherein an excitation band of the second phosphor does not overlap with the fluorescence emission band of the first phosphor.

3. The light source apparatus according to claim 1, wherein the fluorescence emission band of the second phosphor does not overlap with the excitation band of the first phosphor.

4. The light source apparatus according to claim 1, wherein:
   the first irradiation mode is an irradiation mode of performing NBI (Narrow Band Imaging) irradiation,
   the first light emitting element is a light emitting element that performs narrow band light emission, and
   the fluorescence emission band of the first phosphor is a narrower band than the fluorescence emission band of the second phosphor.

5. The light source apparatus according to claim 4, wherein:
   the second irradiation mode is an irradiation mode of performing white color light irradiation by emitting a light of the second irradiation band,
   the second light emitting element is a light emitting element that emits a light included in a blue color band which is a band at a short wavelength side in the second irradiation band, and
   the second phosphor includes the second irradiation band other than the blue color band in the fluorescence emission band, and a light fluorescently emitted is a complementary color for the light emitted by the second light emitting element.

6. The light source apparatus according to claim 5, wherein the first light emitting element and the second light emitting element are semiconductor light emitting elements.

7. The light source apparatus according to claim 6, wherein:
   the first light emitting element is a semiconductor light emitting element having a peak of a light emission intensity at a wavelength close to 415 nm, and
   the first phosphor is a phosphor having a peak of a fluorescence emission intensity at a wavelength close to 540 nm.

8. The light source apparatus according to claim 1, wherein:
   the casing has a printed board and a cylindrical reflector with a bottom surface side being attached onto the printed board, a top surface side of the casing being opened toward the irradiating direction of the light,
   the first light emitting element and the second light emitting element are mounted at positions inward of the reflector on the printed board, and
   the first phosphor and the second phosphor are sealed with a resin provided in a recessed portion defined by the printed board and the reflector so as to cover the first light emitting element and the second light emitting element.

9. An electronic image acquiring apparatus, comprising:
   the light source apparatus according to claim 1; and
   an image pickup apparatus that causes a light irradiated from the light source apparatus and reflected by an object to form an image by an optical system and picks up the image.

10. An electronic image observation apparatus, comprising:
    the electronic image acquiring apparatus according to claim 9; and
    a display apparatus that displays an image picked up by the image pickup apparatus.

11. An endoscope apparatus, comprising:

the electronic image acquiring apparatus according to claim 9; and an insertion portion in which an irradiating optical element for irradiating an object with the light from the light source apparatus, and an observing optical element configuring at least a part of the optical system of the image pickup apparatus are disposed at a distal end side.

12. A capsule endoscope apparatus, comprising:

the electronic image acquiring apparatus according to claim 9; and a capsule casing that houses the electronic image acquiring apparatus.

* * * * *